US012702821B2

(12) United States Patent
Schellenberg et al.

(10) Patent No.: US 12,702,821 B2
(45) Date of Patent: Aug. 11, 2026

(54) IMPLANTABLE DEVICE FOR DETERMINING A FLUID VOLUME FLOW THROUGH A BLOOD VESSEL

(71) Applicant: KARDION GMBH, Stuttgart (DE)

(72) Inventors: Inga Schellenberg, Stuttgart (DE); Thomas Alexander Schlebusch, Renningen (DE); Tobias Schmid, Stuttgart (DE)

(73) Assignee: Kardion GMBH, Stuttgart (DE)

( * ) Notice: Subject to any disclaimer, the term of this patent is extended or adjusted under 35 U.S.C. 154(b) by 1189 days.

(21) Appl. No.: 15/734,821

(22) PCT Filed: Jun. 6, 2019

(86) PCT No.: PCT/EP2019/064782
§ 371 (c)(1),
(2) Date: Jul. 19, 2021

(87) PCT Pub. No.: WO2019/234151
PCT Pub. Date: Dec. 12, 2019

(65) Prior Publication Data

US 2021/0379360 A1 Dec. 9, 2021

(30) Foreign Application Priority Data

Jun. 6, 2018 (DE) ......................... 102018208927.2

(51) Int. Cl.
*A61M 60/546* (2021.01)
*A61M 60/17* (2021.01)
(Continued)

(52) U.S. Cl.
CPC .......... *A61M 60/546* (2021.01); *A61M 60/17* (2021.01); *A61M 60/178* (2021.01);
(Continued)

(58) Field of Classification Search
CPC .. A61M 60/546; A61M 60/17; A61M 60/178; A61M 60/216; A61M 60/523;
(Continued)

(56) References Cited

U.S. PATENT DOCUMENTS 2,254,698 A 9/1941 Hansen, Jr.
3,085,407 A 4/1963 Tomlinson
(Continued)

FOREIGN PATENT DOCUMENTS

CA 3 000 581 4/2017
CA 3 122 415 7/2020
(Continued)

OTHER PUBLICATIONS

Atkinson P, Wells PN. Pulse-Doppler ultrasound and its clinical application. Yale J Biol Med. Jul.-Aug. 1977;50(4):367-73. (Year: 1977).*

(Continued)

*Primary Examiner* — Jennifer Pitrak McDonald
*Assistant Examiner* — Christopher J Mutchler
(74) *Attorney, Agent, or Firm* — Knobbe, Martens, Olson & Bear, LLP

(57) ABSTRACT

The invention relates to an implantable device (1) for determining a fluid volume flow (2) through a blood vessel (3), comprising: —at least one sensor (4) for recording at least one flow parameter, —a retaining means (5) for retaining a vessel wall port (6) in the region of a vessel wall (7) of the blood vessel (3), wherein the retaining means (5) is formed to retain the at least one sensor (4) in the region of the vessel wall (7).

18 Claims, 3 Drawing Sheets

(51) Int. Cl.

| | |
|---|---|
| ***A61M 60/178*** | (2021.01) |
| ***A61M 60/216*** | (2021.01) |
| ***A61M 60/523*** | (2021.01) |
| ***A61M 60/859*** | (2021.01) |
| ***A61M 60/861*** | (2021.01) |
| ***A61M 60/878*** | (2021.01) |

(52) U.S. Cl.
CPC ........ *A61M 60/216* (2021.01); *A61M 60/523* (2021.01); *A61M 60/859* (2021.01); *A61M 60/861* (2021.01); *A61M 60/878* (2021.01); *A61M 2205/3375* (2013.01)

(58) Field of Classification Search
CPC .............. A61M 60/859; A61M 60/861; A61M 60/878; A61M 2205/3375; A61M 60/13; A61M 2039/0258; A61B 8/06; A61B 8/4227
See application file for complete search history.

(56) References Cited

U.S. PATENT DOCUMENTS 3,088,323 A 5/1963 Welkowitz et al.
3,614,181 A 10/1971 Meeks
3,645,268 A 2/1972 Capote
3,747,998 A 7/1973 Klein et al.
3,790,878 A 2/1974 Brokaw
3,807,813 A 4/1974 Milligan
4,023,562 A 5/1977 Hynecek et al.
4,441,210 A 4/1984 Hochmair et al.
4,559,952 A 12/1985 Angelsen et al.
4,680,730 A 7/1987 Omoda
4,781,525 A 11/1988 Hubbard et al.
4,888,009 A 12/1989 Lederman et al.
4,888,011 A 12/1989 Kung et al.
4,889,131 A 12/1989 Salem et al.
4,896,754 A 1/1990 Carlson et al.
4,902,272 A 2/1990 Milder et al.
5,000,177 A 3/1991 Hoffmann et al.
5,045,051 A 9/1991 Milder et al.
5,195,877 A 3/1993 Kletschka
5,269,811 A 12/1993 Hayes
5,289,821 A 3/1994 Swartz
5,443,503 A 8/1995 Yamane
5,456,715 A 10/1995 Liotta
5,527,159 A 6/1996 Bozeman, Jr. et al.
5,581,038 A 12/1996 Lampropoulos
5,599,173 A 2/1997 Chen et al.
5,606,972 A 3/1997 Routh
5,613,935 A 3/1997 Jarvik
5,629,661 A 5/1997 Ooi et al.
5,662,115 A 9/1997 Torp
5,676,651 A 10/1997 Larson, Jr. et al.
5,690,674 A 11/1997 Diaz
5,695,471 A 12/1997 Wampler
5,702,430 A 12/1997 Larson, Jr. et al.
5,713,954 A 2/1998 Rosenberg et al.
5,720,771 A 2/1998 Snell
5,752,976 A 5/1998 Duffin et al.
5,766,207 A 6/1998 Potter et al.
5,814,900 A 9/1998 Esser
5,827,203 A 10/1998 Nita
5,843,141 A 12/1998 Bischoff et al.
5,865,759 A 2/1999 Koblanski
5,888,242 A 3/1999 Antaki et al.
5,904,708 A 5/1999 Goedeke
5,911,685 A 6/1999 Siess et al.
5,964,694 A 10/1999 Siess et al.
5,980,465 A 11/1999 Elgas
5,982,153 A 11/1999 Nagal
6,007,478 A 12/1999 Siess et al.
6,024,704 A 2/2000 Meador et al.
6,053,873 A * 4/2000 Govari ................. A61B 5/0031
600/468
6,058,958 A 5/2000 Benkowski et al.
6,149,405 A 11/2000 Abe et al.
6,167,765 B1 1/2001 Weitzel
6,176,822 B1 1/2001 Nix et al.
6,183,412 B1 2/2001 Benkowsi et al.
6,185,460 B1 2/2001 Thompson
6,190,324 B1 2/2001 Kieval et al.
6,210,318 B1 4/2001 Lederman
6,212,430 B1 4/2001 Kung et al.
6,224,540 B1 5/2001 Lederman et al.
6,231,498 B1 5/2001 Pfeiffer et al.
6,245,007 B1 6/2001 Bedingham et al.
6,254,359 B1 7/2001 Aber
6,264,601 B1 7/2001 Jassawalla et al.
6,314,322 B1 11/2001 Rosenberg
6,324,430 B1 11/2001 Zarinetchi et al.
6,324,431 B1 11/2001 Zarinetchi et al.
6,351,048 B1 2/2002 Schob et al.
6,361,292 B1 3/2002 Chang et al.
6,366,817 B1 4/2002 Kung
6,389,318 B1 5/2002 Zarinetchi et al.
6,398,734 B1 6/2002 Cimochowski et al.
6,400,991 B1 6/2002 Kung
6,432,136 B1 8/2002 Weiss et al.
6,438,409 B1 8/2002 Malik et al.
6,442,434 B1 8/2002 Zarinetchi et al.
6,445,956 B1 9/2002 Laird et al.
6,471,713 B1 10/2002 Vargas et al.
6,496,733 B2 12/2002 Zarinetchi et al.
6,508,756 B1 1/2003 Kung et al.
6,512,949 B1 1/2003 Combs et al.
6,516,227 B1 2/2003 Meadows et al.
6,527,698 B1 3/2003 Kung et al.
6,530,876 B1 3/2003 Spence
6,540,658 B1 4/2003 Fasciano et al.
6,540,659 B1 4/2003 Milbocker
6,553,263 B1 4/2003 Meadows et al.
6,561,975 B1 5/2003 Pool et al.
6,579,257 B1 6/2003 Elgas et al.
6,592,620 B1 7/2003 Lancisi et al.
6,602,182 B1 8/2003 Milbocker
6,605,032 B2 8/2003 Benkowsi et al.
6,652,447 B2 11/2003 Benkowsi et al.
6,731,976 B2 5/2004 Penn et al.
6,879,126 B2 4/2005 Paden et al.
6,912,423 B2 6/2005 Ley et al.
6,949,066 B2 9/2005 Bearnson et al.
6,979,338 B1 12/2005 Loshakove et al.
6,984,201 B2 1/2006 Khaghani et al.
7,010,954 B2 3/2006 Siess
7,022,100 B1 4/2006 Aboul-Hosn et al.
7,024,244 B2 4/2006 Muhlenberg et al.
7,062,331 B2 6/2006 Zarinetchi et al.
7,070,398 B2 7/2006 Olsen et al.
7,070,555 B2 7/2006 Siess
7,083,588 B1 8/2006 Shmulewitz et al.
7,138,776 B1 11/2006 Gauthier et al.
7,155,291 B2 12/2006 Zarinetchi et al.
7,160,243 B2 1/2007 Medvedev
7,175,588 B2 2/2007 Morello
7,177,681 B2 2/2007 Xhu
7,238,151 B2 7/2007 Frazier
7,338,521 B2 3/2008 Antaki et al.
7,396,327 B2 7/2008 Morello
7,513,864 B2 4/2009 Kantrowitz et al.
7,520,850 B2 4/2009 Brockway
7,526,338 B1 4/2009 Gill
7,527,599 B2 5/2009 Hickey
7,591,777 B2 9/2009 LaRose
7,744,560 B2 6/2010 Struble
7,762,941 B2 7/2010 Jarvik
7,794,384 B2 9/2010 Sugiura et al.
7,819,916 B2 10/2010 Yaegashi
7,850,593 B2 12/2010 Vincent et al.
7,850,594 B2 12/2010 Sutton et al.
7,856,335 B2 12/2010 Morello et al.
7,862,501 B2 1/2011 Woodward et al.
7,942,805 B2 5/2011 Shambaugh, Jr.
7,951,062 B2 5/2011 Morello

(56) References Cited

U.S. PATENT DOCUMENTS

| | | | |
|---|---|---|---|
| 7,951,129 | B2 | 5/2011 | Chinchoy |
| 7,959,551 | B2 | 6/2011 | Jarvik |
| 7,963,905 | B2 | 6/2011 | Salmonsen et al. |
| 7,988,728 | B2 | 8/2011 | Ayre |
| 8,012,079 | B2 | 9/2011 | Delgado, III |
| 8,075,472 | B2 | 12/2011 | Zilbershlag et al. |
| 8,088,059 | B2 | 1/2012 | Jarvik |
| 8,190,390 | B2 | 5/2012 | Morello et al. |
| 8,211,028 | B2 | 7/2012 | Karamanoglu et al. |
| 8,231,519 | B2 | 7/2012 | Reichenbach et al. |
| 8,303,482 | B2 | 11/2012 | Schima et al. |
| 8,323,173 | B2 | 12/2012 | Benkowsi et al. |
| 8,435,182 | B1 | 5/2013 | Tamura |
| 8,449,444 | B2 | 5/2013 | Poirier |
| 8,461,817 | B2 | 6/2013 | Martin et al. |
| 8,489,200 | B2 | 7/2013 | Zarinetchi et al. |
| 8,545,380 | B2 | 10/2013 | Farnan et al. |
| 8,585,572 | B2 | 11/2013 | Mehmanesh |
| 8,591,393 | B2 | 11/2013 | Walters et al. |
| 8,594,790 | B2 | 11/2013 | Kjellstrom et al. |
| 8,608,635 | B2 | 12/2013 | Yomtov et al. |
| 8,612,002 | B2 | 12/2013 | Faltys et al. |
| 8,620,447 | B2 | 12/2013 | D'Ambrosio et al. |
| 8,622,949 | B2 | 1/2014 | Zafirelis et al. |
| 8,657,733 | B2 | 2/2014 | Ayre et al. |
| 8,657,875 | B2 | 2/2014 | Kung et al. |
| 8,715,151 | B2 | 5/2014 | Poirier |
| 8,747,293 | B2 | 6/2014 | Arndt et al. |
| 8,766,788 | B2 | 7/2014 | D'Ambrosio |
| 8,827,890 | B2 | 9/2014 | Lee et al. |
| 8,849,398 | B2 | 9/2014 | Evans |
| 8,862,232 | B2 | 10/2014 | Zarinetchi et al. |
| 8,864,643 | B2 | 10/2014 | Reichenbach et al. |
| 8,864,644 | B2 | 10/2014 | Yomtov |
| 8,870,739 | B2 | 10/2014 | LaRose et al. |
| 8,876,685 | B2 | 11/2014 | Crosby et al. |
| 8,882,477 | B2 | 11/2014 | Fritz, IV et al. |
| 8,888,728 | B2 | 11/2014 | Aboul-Hosn et al. |
| 8,897,873 | B2 | 11/2014 | Schima et al. |
| 8,900,114 | B2 | 12/2014 | Tansley et al. |
| 8,903,492 | B2 | 12/2014 | Soykan et al. |
| 8,961,389 | B2 | 2/2015 | Zilbershlag |
| 9,002,468 | B2 | 4/2015 | Shea et al. |
| 9,002,469 | B2 | 4/2015 | D'Ambrosio |
| 9,071,182 | B2 | 6/2015 | Yoshida et al. |
| 9,091,271 | B2 | 7/2015 | Bourque |
| 9,220,826 | B2 | 12/2015 | D'Ambrosio |
| 9,283,314 | B2 | 3/2016 | Prasad et al. |
| 9,297,735 | B2 | 3/2016 | Graichen et al. |
| 9,308,305 | B2 | 4/2016 | Chen et al. |
| 9,345,824 | B2 | 5/2016 | Mohl et al. |
| 9,364,592 | B2 | 6/2016 | McBride |
| 9,371,826 | B2 | 6/2016 | Yanai et al. |
| 9,381,286 | B2 | 7/2016 | Spence et al. |
| 9,427,508 | B2 | 8/2016 | Reyes et al. |
| 9,427,509 | B2 | 8/2016 | Vodermayer |
| 9,440,013 | B2 | 9/2016 | Dowling et al. |
| 9,456,898 | B2 | 10/2016 | Barnes et al. |
| 9,474,840 | B2 | 10/2016 | Siess |
| 9,486,566 | B2 | 11/2016 | Siess |
| 9,492,600 | B2 | 11/2016 | Strueber et al. |
| 9,492,601 | B2 | 11/2016 | Casas et al. |
| 9,511,179 | B2 | 12/2016 | Casas et al. |
| 9,539,094 | B2 | 1/2017 | Dale et al. |
| 9,555,173 | B2 | 1/2017 | Spanier |
| 9,555,175 | B2 | 1/2017 | Bulent et al. |
| 9,556,873 | B2 | 1/2017 | Yanai et al. |
| 9,561,362 | B2 | 2/2017 | Malinowski |
| 9,566,374 | B2 | 2/2017 | Spence et al. |
| 9,569,985 | B2 | 2/2017 | Alkhatib et al. |
| 9,592,397 | B2 | 3/2017 | Hansen et al. |
| 9,603,984 | B2 | 3/2017 | Romero et al. |
| 9,616,107 | B2 | 4/2017 | VanAntwerp et al. |
| 9,636,442 | B2 | 5/2017 | Karmon et al. |
| 9,656,010 | B2 | 5/2017 | Burke |
| 9,669,142 | B2 | 6/2017 | Spanier et al. |
| 9,669,144 | B2 | 6/2017 | Spanier et al. |
| 9,694,123 | B2 | 7/2017 | Bourque et al. |
| 9,713,701 | B2 | 7/2017 | Sarkar et al. |
| 9,717,831 | B2 | 8/2017 | Schuermann |
| 9,724,083 | B2 | 8/2017 | Quadri et al. |
| 9,744,282 | B2 | 8/2017 | Rosenberg et al. |
| 9,789,236 | B2 | 10/2017 | Bonde |
| 9,800,172 | B1 | 10/2017 | Leabman |
| 9,833,314 | B2 | 12/2017 | Corbett |
| 9,833,550 | B2 | 12/2017 | Siess |
| 9,833,611 | B2 | 12/2017 | Govea et al. |
| 9,848,899 | B2 | 12/2017 | Sliwa et al. |
| 9,849,224 | B2 | 12/2017 | Angwin et al. |
| 9,878,087 | B2 | 1/2018 | Richardson et al. |
| 9,943,236 | B2 | 4/2018 | Bennett et al. |
| 9,950,102 | B2 | 4/2018 | Spence et al. |
| 9,974,894 | B2 | 5/2018 | Morello |
| 9,999,714 | B2 | 6/2018 | Spanier et al. |
| 10,010,412 | B2 | 7/2018 | Taft |
| 10,010,662 | B2 | 7/2018 | Wiesener et al. |
| 10,022,480 | B2 | 7/2018 | Greatrex et al. |
| 10,029,037 | B2 | 7/2018 | Muller et al. |
| 10,052,420 | B2 | 8/2018 | Medvedev et al. |
| 10,143,571 | B2 | 12/2018 | Spence et al. |
| 10,148,126 | B2 | 12/2018 | Hoarau |
| 10,279,093 | B2 | 5/2019 | Reichenbach et al. |
| 10,322,217 | B2 | 6/2019 | Spence |
| 10,342,906 | B2 | 7/2019 | D'Ambrosio et al. |
| 10,350,342 | B2 | 7/2019 | Thomas et al. |
| 10,357,598 | B2 | 7/2019 | Aboul-Hosn et al. |
| 10,376,162 | B2 | 8/2019 | Edelman et al. |
| 10,413,651 | B2 | 9/2019 | Yomtov et al. |
| 10,426,879 | B2 | 10/2019 | Farnan |
| 10,449,275 | B2 | 10/2019 | Corbett |
| 10,463,508 | B2 | 11/2019 | Spence et al. |
| 10,500,322 | B2 | 12/2019 | Karch |
| 10,525,178 | B2 | 1/2020 | Zeng |
| 10,549,020 | B2 | 2/2020 | Spence et al. |
| 10,561,771 | B2 | 2/2020 | Heilman et al. |
| 10,561,772 | B2 | 2/2020 | Schumacher |
| 10,561,773 | B2 | 2/2020 | Ferrari et al. |
| 10,632,241 | B2 | 4/2020 | Schenck et al. |
| 10,660,998 | B2 | 5/2020 | Hodges |
| 10,668,195 | B2 | 6/2020 | Flores |
| 10,732,583 | B2 | 8/2020 | Rudser |
| 10,857,275 | B2 | 12/2020 | Granegger |
| 10,864,308 | B2 | 12/2020 | Muller et al. |
| 10,944,293 | B2 | 3/2021 | Nakao |
| 11,000,282 | B2 | 5/2021 | Schuelke et al. |
| 11,027,114 | B2 | 6/2021 | D'Ambrosio et al. |
| RE48,649 | E | 7/2021 | Siess |
| 11,056,878 | B2 | 7/2021 | Gao et al. |
| 11,065,437 | B2 | 7/2021 | Aber et al. |
| 11,067,085 | B2 | 7/2021 | Granegger et al. |
| 11,071,857 | B2 | 7/2021 | Sun |
| 11,103,715 | B2 | 8/2021 | Fort |
| 11,110,265 | B2 | 9/2021 | Johnson |
| 11,120,908 | B2 | 9/2021 | Agnello et al. |
| 11,121,580 | B2 | 9/2021 | Partovi |
| 11,131,968 | B2 | 9/2021 | Rudser |
| 11,147,960 | B2 | 10/2021 | Spanier et al. |
| 11,154,701 | B2 | 10/2021 | Reyes et al. |
| 11,154,702 | B2 | 10/2021 | Kadrolkar et al. |
| 11,179,559 | B2 | 11/2021 | Hansen |
| 11,185,682 | B2 | 11/2021 | Farnan |
| 11,191,945 | B2 | 12/2021 | Siess et al. |
| 11,197,618 | B2 | 12/2021 | Edelman et al. |
| 11,217,344 | B2 | 1/2022 | Agnello |
| 11,224,737 | B2 | 1/2022 | Petersen et al. |
| 11,235,139 | B2 | 2/2022 | Kudlik |
| 11,241,572 | B2 | 2/2022 | Dague et al. |
| 11,266,502 | B1 | 3/2022 | Wallace |
| 11,273,299 | B2 | 3/2022 | Wolman et al. |
| 11,285,310 | B2 | 3/2022 | Curran et al. |
| 11,285,311 | B2 | 3/2022 | Siess et al. |
| 11,291,826 | B2 | 4/2022 | Tuval et al. |
| 11,298,524 | B2 | 4/2022 | El Katerji et al. |
| 11,311,711 | B2 | 4/2022 | Casas et al. |

(56) References Cited

U.S. PATENT DOCUMENTS 11,316,371 B1 4/2022 Partovi et al.
11,316,679 B2 4/2022 Agnello
11,317,988 B2 5/2022 Hansen et al.
11,320,382 B2 5/2022 Aikawa
11,324,395 B2 5/2022 Banik et al.
11,331,082 B2 5/2022 Itoh et al.
11,337,724 B2 5/2022 Masubuchi et al.
11,338,125 B2 5/2022 Liu et al.
11,344,717 B2 5/2022 Kallenbach et al.
11,351,356 B2 6/2022 Mohl
11,351,357 B2 6/2022 Mohl
11,351,358 B2 6/2022 Nix et al.
11,351,359 B2 6/2022 Clifton et al.
11,351,360 B2 6/2022 Rudser et al.
11,357,438 B2 6/2022 Stewart et al.
11,357,968 B2 6/2022 El Katerji et al.
11,368,081 B2 6/2022 Vogt et al.
11,369,785 B2 6/2022 Callaway et al.
11,369,786 B2 6/2022 Menon et al.
11,376,415 B2 7/2022 Mohl
11,376,419 B2 7/2022 Reyes et al.
11,389,639 B2 7/2022 Casas
11,389,641 B2 7/2022 Nguyen et al.
11,406,483 B2 8/2022 Wirbisky et al.
11,406,520 B2 8/2022 Lam
11,406,802 B2 8/2022 DeGraaf et al.
11,413,443 B2 8/2022 Hodges et al.
11,413,444 B2 8/2022 Nix et al.
11,413,445 B2 8/2022 Brown et al.
11,420,041 B2 8/2022 Karch
11,439,806 B2 9/2022 Kimball et al.
11,446,481 B2 9/2022 Wolman et al.
11,471,692 B2 10/2022 Aghassian et al.
11,478,629 B2 10/2022 Harjes et al.
11,497,906 B2 11/2022 Grace et al.
11,517,737 B2 12/2022 Struthers et al.
11,517,738 B2 12/2022 Wisniewski
11,517,740 B2 12/2022 Agarwa et al.
11,521,723 B2 12/2022 Liu et al.
11,524,165 B2 12/2022 Tan et al.
11,527,322 B2 12/2022 Agnello et al.
11,529,062 B2 12/2022 Moyer et al.
11,529,508 B2 12/2022 Jablonsk et al.
11,554,260 B2 1/2023 Reyes et al.
11,572,879 B2 2/2023 Mohl
11,574,741 B2 2/2023 Tan et al.
11,577,068 B2 2/2023 Spence et al.
11,581,083 B2 2/2023 El Katerji et al.
11,583,659 B2 2/2023 Pfeffer et al.
11,583,671 B2 2/2023 Nguyen et al.
11,587,337 B2 2/2023 Lemay et al.
11,590,337 B2 2/2023 Granegger et al.
11,596,727 B2 3/2023 Siess et al.
11,602,624 B2 3/2023 Siess et al.
11,616,397 B2 3/2023 Schilling
11,622,695 B1 4/2023 Adriola et al.
11,628,293 B2 4/2023 Gandhi et al.
11,639,722 B2 5/2023 Medvedev et al.
11,642,512 B2 5/2023 Schilling
11,648,386 B2 5/2023 Poirer
11,653,841 B2 5/2023 Reyes et al.
11,666,746 B2 6/2023 Ferrari et al.
11,668,321 B2 6/2023 Richert et al.
11,674,517 B2 6/2023 Mohl
11,676,718 B2 6/2023 Agnello et al.
11,682,924 B2 6/2023 Hansen et al.
11,684,276 B2 6/2023 Cros et al.
11,684,769 B2 6/2023 Harjes et al.
11,689,057 B2 6/2023 Hansen
11,694,539 B2 7/2023 Kudlik et al.
11,694,813 B2 7/2023 El Katerji et al.
11,696,782 B2 7/2023 Carlson et al.
11,699,551 B2 7/2023 Diekhans et al.
11,707,617 B2 7/2023 Reyes et al.
11,712,167 B2 8/2023 Medvedev et al.
11,724,091 B2 8/2023 Siess et al.
11,745,005 B2 9/2023 Delgado, III
11,752,354 B2 9/2023 Stotz et al.
11,754,077 B1 9/2023 Mohl
D1,001,145 S 10/2023 Lussier et al.
D1,001,146 S 10/2023 Lussier et al.
11,771,885 B2 10/2023 Liu et al.
11,779,234 B2 10/2023 Harjes et al.
11,781,551 B2 10/2023 Yanai et al.
11,790,487 B2 10/2023 Barbato et al.
11,793,994 B2 10/2023 Josephy et al.
11,804,767 B2 10/2023 Vogt et al.
11,806,116 B2 11/2023 Tuval et al.
11,806,517 B2 11/2023 Petersen
11,806,518 B2 11/2023 Michelena et al.
11,813,079 B2 11/2023 Lau et al.
11,818,782 B2 11/2023 Doudian et al.
11,824,381 B2 11/2023 Conyers et al.
11,826,127 B2 11/2023 Casas
11,832,793 B2 12/2023 McWeeney et al.
11,832,868 B2 12/2023 Smail et al.
11,837,364 B2 12/2023 Lee et al.
11,844,592 B2 12/2023 Tuval et al.
11,844,940 B2 12/2023 D'Ambrosio et al.
11,850,073 B2 12/2023 Wright et al.
11,850,414 B2 12/2023 Schenck et al.
11,850,415 B2 12/2023 Schwammenthal et al.
D1,012,284 S 1/2024 Glaser et al.
11,857,345 B2 1/2024 Hanson et al.
11,864,878 B2 1/2024 Duval et al.
11,872,384 B2 1/2024 Cotter
11,881,721 B2 1/2024 Araujo et al.
11,883,207 B2 1/2024 El Katerji et al.
D1,014,552 S 2/2024 Lussier et al.
11,890,082 B2 2/2024 Cros et al.
11,896,199 B2 2/2024 Lent et al.
11,900,660 B2 2/2024 Saito et al.
11,903,657 B2 2/2024 Geric et al.
11,906,411 B2 2/2024 Graichen et al.
11,911,550 B2 2/2024 Itamochi et al.
D1,017,634 S 3/2024 Lussier et al.
D1,017,699 S 3/2024 Moore et al.
11,923,078 B2 3/2024 Fallen et al.
11,923,093 B2 3/2024 Moffitt et al.
11,925,794 B2 3/2024 Malkin et al.
11,931,073 B2 3/2024 Walsh et al.
11,931,528 B2 3/2024 Rohl et al.
11,931,588 B2 3/2024 Aghassian
11,986,274 B2 5/2024 Edelman
11,996,699 B2 5/2024 Vasconcelos Araujo et al.
12,017,076 B2 6/2024 Tan et al.
12,023,476 B2 7/2024 Tuval et al.
12,029,891 B2 7/2024 Siess et al.
12,059,559 B2 8/2024 Muller et al.
D1,043,730 S 9/2024 Lussier et al.
D1,043,731 S 9/2024 Lussier et al.
12,076,544 B2 9/2024 Siess et al.
12,097,016 B2 9/2024 Goldvasser
12,102,815 B2 10/2024 Dhaliwal et al.
12,102,835 B2 10/2024 Stotz et al.
12,144,650 B2 11/2024 Spanier et al.
12,144,976 B2 11/2024 Baumbach et al.
12,150,647 B2 11/2024 Schuelke et al.
12,178,554 B2 12/2024 Stotz et al.
12,179,009 B2 12/2024 El Katerji et al.
12,183,459 B2 12/2024 Agnello et al.
12,194,287 B2 1/2025 Kassel et al.
12,201,821 B2 1/2025 Schlebusch et al.
12,211,615 B2 1/2025 Nix et al.
D1,060,379 S 2/2025 Lussier et al.
12,213,771 B2 2/2025 Curran et al.
12,217,850 B2 2/2025 Agnello
12,222,267 B2 2/2025 Stotz et al.
12,230,868 B2 2/2025 Wenning et al.
12,233,250 B2 2/2025 Stotz et al.
12,251,551 B2 3/2025 Liu et al.
12,257,424 B2 3/2025 Schlebusch et al.
12,268,861 B2 4/2025 D'Ambrosio et al.
12,296,158 B2 5/2025 Higgins et al.

(56) References Cited

U.S. PATENT DOCUMENTS 12,296,159 B2 5/2025 Schilling et al.
12,310,621 B2 5/2025 Murphy
12,310,708 B2 5/2025 Schlebusch et al.
12,311,160 B2 5/2025 Schlebusch et al.
12,324,906 B2 6/2025 Baumbach et al.
12,329,501 B2 6/2025 Moyer et al.
12,329,956 B2 6/2025 Sunagawa
12,329,959 B2 6/2025 Hassan et al.
12,343,518 B2 7/2025 Tuval et al.
D1,090,610 S 8/2025 Kroeker et al.
12,377,256 B2 8/2025 Stotz et al.
12,390,168 B2 8/2025 Katerji et al.
12,397,099 B2 8/2025 Germain et al.
12,397,147 B2 8/2025 Siess et al.
12,400,788 B2 8/2025 Diekhans et al.
D1,092,492 S 9/2025 Lussier et al.
12,403,296 B2 9/2025 Baumbach et al.
12,409,313 B2 9/2025 Eggen et al.
12,424,306 B2 9/2025 Liu et al.
12,424,315 B2 9/2025 Nix et al.
12,434,060 B2 10/2025 Tan et al.
12,440,665 B2 10/2025 Tuval et al.
12,445,278 B2 10/2025 Agnello
12,451,230 B2 10/2025 El Katerji et al.
12,453,847 B2 10/2025 Sa
12,476,002 B2 11/2025 El Katerji et al.
12,476,488 B2 11/2025 Araujo et al.
12,478,266 B2 11/2025 Edelman et al.
12,478,267 B2 11/2025 Schlebusch et al.
12,478,774 B2 11/2025 Muller
12,491,357 B2 12/2025 Baumbach et al.
12,494,292 B2 12/2025 El Katerji et al.
12,502,524 B2 12/2025 Stigloher et al.
12,508,418 B2 12/2025 Baumbach et al.
12,521,543 B2 1/2026 Egler
2001/0016686 A1* 8/2001 Okada .................. A61B 8/0858 600/454
2001/0037093 A1 11/2001 Benkowski et al.
2001/0039828 A1 11/2001 Shin et al.
2002/0022785 A1 2/2002 Romano
2002/0082585 A1 6/2002 Carroll et al.
2002/0093412 A1 7/2002 Morrison
2002/0147495 A1 10/2002 Petroff
2002/0151761 A1 10/2002 Viole et al.
2002/0177324 A1 11/2002 Metzler
2003/0040765 A1 2/2003 Breznock
2003/0069465 A1 4/2003 Benkowski et al.
2003/0125766 A1 7/2003 Ding
2003/0130581 A1 7/2003 Salo et al.
2003/0139643 A1 7/2003 Smith et al.
2003/0167002 A1 9/2003 Nagar et al.
2003/0191357 A1 10/2003 Frazier
2003/0199727 A1 10/2003 Burke
2004/0022640 A1 2/2004 Siess et al.
2004/0034411 A1 2/2004 Quijano
2004/0044266 A1 3/2004 Siess et al.
2004/0065143 A1 4/2004 Husher
2004/0124979 A1 7/2004 Medema
2004/0130009 A1 7/2004 Tangpuz
2004/0167376 A1 8/2004 Peters et al.
2004/0167410 A1 8/2004 Hettrick
2004/0225177 A1 11/2004 Coleman et al.
2004/0241019 A1 12/2004 Goldowsky
2004/0260346 A1 12/2004 Overall et al.
2005/0001324 A1 1/2005 Dunn
2005/0006083 A1 1/2005 Chen et al.
2005/0019167 A1 1/2005 Nusser et al.
2005/0046044 A1 3/2005 Theuss
2005/0107658 A1 5/2005 Brockway
2005/0107847 A1 5/2005 Gruber et al.
2005/0126268 A1 6/2005 Ouriev et al.
2005/0267322 A1 12/2005 LaRose
2006/0004423 A1 1/2006 Boveja et al.
2006/0030809 A1 2/2006 Barzilay et al.
2006/0108697 A1 5/2006 Wang
2006/0108901 A1 5/2006 Mao-Chin
2006/0122583 A1 6/2006 Pesach et al.
2006/0190036 A1 8/2006 Wendel et al.
2006/0196277 A1 9/2006 Allen et al.
2006/0217785 A1 9/2006 Matei
2006/0229488 A1 10/2006 Ayre et al.
2006/0287600 A1 12/2006 McEowen
2006/0287604 A1 12/2006 Hickey
2007/0060787 A1 3/2007 Peters et al.
2007/0069354 A1 3/2007 Dangelmaier
2007/0073352 A1 3/2007 Euler et al.
2007/0088214 A1 4/2007 Shuros et al.
2007/0129767 A1 6/2007 Wahlstrand
2007/0156006 A1 7/2007 Smith et al.
2007/0255352 A1 11/2007 Roline et al.
2007/0266778 A1 11/2007 Corey et al.
2007/0282209 A1 12/2007 Lui et al.
2007/0299325 A1 12/2007 Farrell et al.
2008/0015481 A1 1/2008 Bergin et al.
2008/0015517 A1 1/2008 Geistert et al.
2008/0079392 A1 4/2008 Baarman et al.
2008/0082005 A1 4/2008 Stern et al.
2008/0091239 A1 4/2008 Johansson et al.
2008/0097595 A1 4/2008 Gabbay
2008/0102096 A1 5/2008 Molin et al.
2008/0108901 A1 5/2008 Baba et al.
2008/0108930 A1 5/2008 Weitzel et al.
2008/0133006 A1 6/2008 Crosby et al.
2008/0146996 A1 6/2008 Smisson
2008/0210016 A1 9/2008 Zwirn et al.
2008/0211455 A1 9/2008 Park et al.
2008/0238364 A1 10/2008 Weber
2008/0248614 A1 10/2008 Yang
2008/0262289 A1 10/2008 Goldowsky
2008/0262361 A1 10/2008 Gutfinger et al.
2008/0266922 A1 10/2008 Mumtaz et al.
2008/0269822 A1 10/2008 Ljungstrom et al.
2008/0275339 A1 11/2008 Thiemann et al.
2008/0287799 A1 11/2008 Hall
2008/0306328 A1 12/2008 Ercolani
2009/0004037 A1 1/2009 Ito
2009/0010462 A1 1/2009 Ekchian et al.
2009/0024042 A1 1/2009 Nunez et al.
2009/0025459 A1 1/2009 Zhang et al.
2009/0064755 A1 3/2009 Fleischli et al.
2009/0105799 A1 4/2009 Hekmat et al.
2009/0131765 A1 5/2009 Roschak et al.
2009/0134711 A1 5/2009 Issa et al.
2009/0198307 A1 8/2009 Mi et al.
2009/0198312 A1 8/2009 Barker
2009/0204163 A1 8/2009 Shuros et al.
2009/0212637 A1 8/2009 Baarman et al.
2009/0226328 A1 9/2009 Morello
2009/0276016 A1 11/2009 Phillips et al.
2009/0312650 A1 12/2009 Maile et al.
2010/0010354 A1 1/2010 Skerl et al.
2010/0010582 A1 1/2010 Carbunaru
2010/0082099 A1 4/2010 Vodermayer et al.
2010/0087742 A1 4/2010 Bishop et al.
2010/0160801 A1 6/2010 Takatani et al.
2010/0191035 A1 7/2010 Kang et al.
2010/0219967 A1 9/2010 Kaufmann
2010/0222632 A1 9/2010 Poirier
2010/0222633 A1 9/2010 Poirier
2010/0222635 A1 9/2010 Poirier
2010/0222878 A1 9/2010 Poirier
2010/0268017 A1 10/2010 Siess
2010/0280568 A1 11/2010 Bulkes et al.
2010/0298625 A1 11/2010 Reichenbach et al.
2010/0312310 A1 12/2010 Meskens
2010/0324378 A1 12/2010 Tran et al.
2010/0331918 A1 12/2010 Digiore et al.
2010/0331920 A1 12/2010 Digiore et al.
2011/0004075 A1 1/2011 Stahmann et al.
2011/0004278 A1 1/2011 Aghassian
2011/0022057 A1 1/2011 Eigler et al.
2011/0034874 A1 2/2011 Reitan
2011/0071336 A1 3/2011 Yomtov
2011/0137394 A1 6/2011 Lunsford et al.

(56) References Cited

U.S. PATENT DOCUMENTS

2011/0144744 A1 6/2011 Wampler
2011/0160516 A1 6/2011 Dague
2011/0172505 A1 7/2011 Kim
2011/0184301 A1 7/2011 Holmstrom
2011/0186943 A1 8/2011 Pahl
2011/0196452 A1 8/2011 Forsell
2011/0218435 A1 9/2011 Srinivasan et al.
2011/0224720 A1 9/2011 Kassab et al.
2011/0230068 A1 9/2011 Pahl
2012/0019201 A1 1/2012 Peterson
2012/0022645 A1 1/2012 Burke
2012/0029408 A1 2/2012 Beaudin
2012/0050931 A1 3/2012 Terry et al.
2012/0068691 A1 3/2012 Ejury
2012/0084024 A1 4/2012 Norcross, Jr.
2012/0112543 A1 5/2012 van Wageningen et al.
2012/0150089 A1 6/2012 Penka et al.
2012/0150291 A1 6/2012 Aber
2012/0158074 A1 6/2012 Hall
2012/0197141 A1 8/2012 Vanney
2012/0203476 A1 8/2012 Dam
2012/0212178 A1 8/2012 Kim
2012/0235633 A1 9/2012 Kesler et al.
2012/0245404 A1 9/2012 Smith
2012/0247200 A1 10/2012 Ahonen et al.
2012/0310037 A1 12/2012 Choi et al.
2012/0330214 A1 12/2012 Peters et al.
2013/0041204 A1 2/2013 Heilman et al.
2013/0046129 A1 2/2013 Medvedev et al.
2013/0066141 A1 3/2013 Doerr et al.
2013/0069651 A1 3/2013 Lumiani
2013/0072846 A1 3/2013 Heide et al.
2013/0099585 A1 4/2013 Von Novak et al.
2013/0116575 A1 5/2013 Mickle et al.
2013/0144379 A1 6/2013 Najafi et al.
2013/0178915 A1 7/2013 Radziemski
2013/0280692 A1 10/2013 Gourlay
2013/0289334 A1 10/2013 Badstibner
2013/0289376 A1 10/2013 Lang
2013/0303831 A1 11/2013 Evans
2013/0303970 A1 11/2013 Keenan et al.
2013/0304404 A1 11/2013 Dam
2014/0005467 A1 1/2014 Farnan et al.
2014/0012282 A1 1/2014 Fritsch
2014/0013852 A1 1/2014 Brown et al.
2014/0028107 A1 1/2014 Kwon
2014/0030122 A1 1/2014 Ozaki
2014/0039587 A1 2/2014 Romero
2014/0063666 A1 3/2014 Kallal et al.
2014/0094645 A1 4/2014 Lafontaine et al.
2014/0100414 A1 4/2014 Tamez et al.
2014/0104898 A1 4/2014 Yeo et al.
2014/0107754 A1 4/2014 Fuhs et al.
2014/0114202 A1 4/2014 Hein et al.
2014/0128659 A1 5/2014 Heuring et al.
2014/0135884 A1 5/2014 Tockman et al.
2014/0194058 A1 7/2014 Lee et al.
2014/0200389 A1 7/2014 Yanai et al.
2014/0233184 A1 8/2014 Thompson et al.
2014/0243688 A1 8/2014 Caron et al.
2014/0249603 A1 9/2014 Yan et al.
2014/0265620 A1 9/2014 Hoarau et al.
2014/0275720 A1 9/2014 Ferrari
2014/0275727 A1 9/2014 Bonde
2014/0296677 A1 10/2014 McEowen
2014/0303426 A1 10/2014 Kerkhoffs et al.
2014/0342203 A1 11/2014 Elian
2014/0346884 A1 11/2014 Fujita
2015/0008755 A1 1/2015 Sone
2015/0027224 A1 1/2015 Schiffer
2015/0028805 A1 1/2015 Dearden et al.
2015/0032007 A1 1/2015 Ottevanger et al.
2015/0080743 A1 3/2015 Siess
2015/0090372 A1 4/2015 Branagan et al.
2015/0141832 A1 5/2015 Yu et al.
2015/0141842 A1 5/2015 Spanier et al.
2015/0157216 A1 6/2015 Stigall et al.
2015/0174307 A1 6/2015 Eckman et al.
2015/0190092 A1 7/2015 Mori
2015/0196076 A1 7/2015 Billingslea
2015/0200562 A1 7/2015 Kilinc et al.
2015/0201900 A1 7/2015 Syed
2015/0244166 A1 8/2015 Chen
2015/0250935 A1 9/2015 Anderson et al.
2015/0273184 A1 10/2015 Scott et al.
2015/0290372 A1* 10/2015 Muller ................ A61M 60/174 600/16
2015/0290373 A1 10/2015 Rudser et al.
2015/0306290 A1 10/2015 Rosenberg et al.
2015/0306291 A1 10/2015 Bonde et al.
2015/0307344 A1 10/2015 Ernst
2015/0327921 A1 11/2015 Govari
2015/0333532 A1 11/2015 Han et al.
2015/0335804 A1 11/2015 Marseille et al.
2015/0365738 A1 12/2015 Purvis et al.
2015/0380972 A1 12/2015 Fort
2016/0000983 A1 1/2016 Mohl et al.
2016/0008531 A1 1/2016 Wang et al.
2016/0022889 A1 1/2016 Bluvshtein et al.
2016/0022890 A1 1/2016 Schwammenthal et al.
2016/0045165 A1 2/2016 Braido et al.
2016/0067395 A1 3/2016 Jimenez et al.
2016/0081680 A1 3/2016 Taylor
2016/0087558 A1 3/2016 Yamamoto
2016/0095968 A1 4/2016 Rudser
2016/0101230 A1 4/2016 Ochsner et al.
2016/0144166 A1 5/2016 Decré et al.
2016/0151553 A1 6/2016 Bonde
2016/0166747 A1 6/2016 Frazier et al.
2016/0175501 A1 6/2016 Schuermann
2016/0213828 A1 7/2016 Sievers
2016/0226296 A1 8/2016 Bae
2016/0250399 A1 9/2016 Tiller et al.
2016/0268846 A1 9/2016 Akuzawa et al.
2016/0271309 A1 9/2016 Throckmorton et al.
2016/0278856 A1 9/2016 Panescu
2016/0302672 A1 10/2016 Kuri
2016/0303299 A1 10/2016 Muller
2016/0317043 A1 11/2016 Campo
2016/0331980 A1 11/2016 Strommer et al.
2016/0336811 A1 11/2016 Liu
2016/0338629 A1 11/2016 Doerr
2016/0344302 A1 11/2016 Inoue
2017/0010144 A1 1/2017 Lenner et al.
2017/0018967 A1 1/2017 Berkhout
2017/0021070 A1 1/2017 Petersen
2017/0043170 A1 2/2017 Guardiani
2017/0047781 A1 2/2017 Stanislawski et al.
2017/0049945 A1 2/2017 Halvorsen et al.
2017/0070082 A1 3/2017 Zheng et al.
2017/0086780 A1 3/2017 Sokulin et al.
2017/0098491 A1 4/2017 Ziaie et al.
2017/0112985 A1 4/2017 Yomtov
2017/0128646 A1 5/2017 Karch
2017/0136164 A1 5/2017 Yeatts
2017/0143977 A1 5/2017 Kaib et al.
2017/0202575 A1* 7/2017 Stanfield ............. A61M 60/216
2017/0203104 A1 7/2017 Nageri et al.
2017/0224279 A1 8/2017 Cahan et al.
2017/0231717 A1 8/2017 Forsell
2017/0239407 A1 8/2017 Hayward
2017/0258980 A1 9/2017 Katsuki et al.
2017/0258981 A1 9/2017 Franano
2017/0271919 A1 9/2017 Von Novak, III et al.
2017/0275799 A1 9/2017 Chen
2017/0288448 A1 10/2017 Kranz et al.
2017/0303375 A1 10/2017 Woodhead
2017/0340789 A1 11/2017 Bonde et al.
2017/0347229 A1 11/2017 Kwon
2017/0348470 A1 12/2017 D'Ambrosio et al.
2017/0353053 A1 12/2017 Muratov
2017/0354812 A1 12/2017 Callaghan et al.
2017/0361115 A1 12/2017 Aghassian
2017/0361117 A1 12/2017 Aghassian

(56) References Cited

U.S. PATENT DOCUMENTS

2018/0021497 A1 1/2018 Nunez
2018/0064860 A1 3/2018 Nunez et al.
2018/0078159 A1 3/2018 Edelman et al.
2018/0078329 A1 3/2018 Hansen et al.
2018/0093070 A1 4/2018 Cottone
2018/0110910 A1 4/2018 Rodemerk et al.
2018/0126053 A1 5/2018 Zilbershlag et al.
2018/0194236 A1 7/2018 Elshaer et al.
2018/0199635 A1 7/2018 Longinotti-Buitoni et al.
2018/0207336 A1 7/2018 Solem
2018/0250457 A1 9/2018 Morello et al.
2018/0256796 A1 9/2018 Hansen
2018/0256800 A1 9/2018 Conyers et al.
2018/0264182 A1 9/2018 Spanier et al.
2018/0269724 A1 9/2018 Smith
2018/0269930 A1 9/2018 Kwon
2018/0278099 A1 9/2018 Hong
2018/0280598 A1 10/2018 Curran et al.
2018/0280708 A1 10/2018 Escalona et al.
2018/0287405 A1 10/2018 Govindaraj
2018/0316209 A1 11/2018 Gliner
2018/0326131 A1 11/2018 Muller et al.
2018/0333059 A1 11/2018 Casas
2018/0353667 A1 12/2018 Moyer et al.
2018/0369469 A1 12/2018 Le Duc De Lillers et al.
2019/0001038 A1 1/2019 Yomtov et al.
2019/0004037 A1 1/2019 Zhang et al.
2019/0054223 A1 2/2019 Frazier et al.
2019/0060543 A1 2/2019 Khanal et al.
2019/0068004 A1 2/2019 Louis
2019/0074726 A1 3/2019 Hosotani
2019/0083690 A1 3/2019 Siess et al.
2019/0097447 A1 3/2019 Partovi
2019/0120905 A1 4/2019 Wong
2019/0175808 A1 6/2019 Zilbershlag et al.
2019/0192752 A1 6/2019 Tiller et al.
2019/0192753 A1 6/2019 Liu et al.
2019/0209755 A1 7/2019 Nix et al.
2019/0209758 A1 7/2019 Tuval et al.
2019/0216995 A1 7/2019 Kapur et al.
2019/0217002 A1 7/2019 Urakabe
2019/0222064 A1 7/2019 Du et al.
2019/0223877 A1 7/2019 Nitzen et al.
2019/0231523 A1 8/2019 Lombardi
2019/0240680 A1 8/2019 Hayakawa
2019/0254543 A1 8/2019 Hartholt et al.
2019/0267913 A1 8/2019 Lim
2019/0282741 A1 9/2019 Franano et al.
2019/0282744 A1 9/2019 D'Ambrosio et al.
2019/0305613 A1 10/2019 Oshima
2019/0344000 A1 11/2019 Kushwaha et al.
2019/0351117 A1 11/2019 Cambronne et al.
2019/0351118 A1 11/2019 Graichen et al.
2019/0351120 A1 11/2019 Kushwaha et al.
2019/0393735 A1 12/2019 Lee et al.
2020/0016309 A1 1/2020 Kallenbach et al.
2020/0022811 A1 1/2020 Griswold
2020/0023109 A1 1/2020 Epple
2020/0028376 A1 1/2020 Ha
2020/0038567 A1 2/2020 Siess et al.
2020/0054806 A1 2/2020 Sun
2020/0060559 A1 2/2020 Edelman et al.
2020/0069857 A1 3/2020 Schwammenthal et al.
2020/0136421 A1 4/2020 Kim
2020/0139032 A1 5/2020 Bryson et al.
2020/0147283 A1 5/2020 Tanner et al.
2020/0164125 A1 5/2020 Muller et al.
2020/0164126 A1 5/2020 Muller
2020/0227954 A1 7/2020 Ding et al.
2020/0253583 A1 8/2020 Brisken et al.
2020/0312450 A1 10/2020 Agnello et al.
2020/0350812 A1 11/2020 Vogt et al.
2020/0366121 A1 11/2020 Guedon
2020/0373768 A1 11/2020 Danilovic
2021/0052793 A1 2/2021 Struthers et al.
2021/0057804 A1 2/2021 Wenning
2021/0143688 A1 5/2021 Agrawal et al.
2021/0268264 A1 9/2021 Stotz
2021/0290087 A1 9/2021 Schlebusch
2021/0290930 A1 9/2021 Kasel
2021/0290931 A1 9/2021 Baumbach
2021/0290933 A1 9/2021 Stotz
2021/0290939 A1 9/2021 Baumbach
2021/0322011 A1 10/2021 Schuelke et al.
2021/0336484 A1 10/2021 Araujo et al.
2021/0339002 A1 11/2021 Schlebusch et al.
2021/0339004 A1 11/2021 Schlebusch et al.
2021/0346674 A1 11/2021 Baumbach et al.
2021/0346675 A1 11/2021 Schlebusch et al.
2021/0346676 A1 11/2021 Schlebusch et al.
2021/0346677 A1 11/2021 Baumbach et al.
2021/0346678 A1 11/2021 Baumbach et al.
2021/0378523 A1 12/2021 Budde
2021/0379359 A1 12/2021 Schellenberg
2021/0386990 A1 12/2021 Stotz et al.
2021/0393944 A1 12/2021 Wenning
2021/0399582 A1 12/2021 Araujo et al.
2022/0016411 A1 1/2022 Winterwerber
2022/0032032 A1 2/2022 Schlebusch et al.
2022/0032036 A1 2/2022 Baumbach et al.
2022/0039669 A1 2/2022 Schlebusch et al.
2022/0047173 A1 2/2022 Stotz et al.
2022/0050037 A1 2/2022 Stotz et al.
2022/0072298 A1 3/2022 Spanier et al.
2022/0076807 A1 3/2022 Agnello
2022/0079457 A1 3/2022 Tuval et al.
2022/0080184 A1 3/2022 Clifton et al.
2022/0080185 A1 3/2022 Clifton et al.
2022/0103023 A1 3/2022 Govindaraj
2022/0105339 A1 4/2022 Nix et al.
2022/0126085 A1 4/2022 Farnan
2022/0126086 A1 4/2022 Schlebusch et al.
2022/0142462 A1 5/2022 Douk et al.
2022/0161019 A1 5/2022 Mitze et al.
2022/0161021 A1 5/2022 Mitze et al.
2022/0166253 A1 5/2022 Forsell
2022/0320901 A1 10/2022 Araujo et al.
2022/0361762 A1 11/2022 Lalancette
2022/0417673 A1 12/2022 Narampanawe
2023/0145482 A1 5/2023 Garrigue
2023/0173250 A1 6/2023 Stigloher
2023/0191141 A1 6/2023 Wenning et al.
2023/0258694 A1 8/2023 Vijayakumar
2023/0352236 A1 11/2023 Diekhans et al.
2023/0381526 A1 11/2023 Stotz et al.
2024/0011808 A1 1/2024 Winzer et al.
2024/0074828 A1 3/2024 Wenning
2024/0186828 A1 6/2024 Chu
2024/0245902 A1 7/2024 Schlebusch et al.
2024/0269459 A1 8/2024 Schellenberg et al.
2024/0312433 A1 9/2024 Kim
2025/0032773 A1 1/2025 Baumbach et al.
2025/0121177 A1 4/2025 West
2025/0134652 A1 5/2025 Maiorano
2025/0143587 A1 5/2025 Stotz
2025/0144397 A1 5/2025 Kassel et al.
2025/0222247 A1 7/2025 Schlebusch
2025/0235687 A1 7/2025 Schlebusch et al.
2025/0251330 A1 8/2025 Stotz
2025/0281060 A1 9/2025 Schlebusch et al.
2025/0319299 A1 10/2025 Stotz et al.
2025/0345590 A1 11/2025 Schlebusch et al.
2025/0367429 A1 12/2025 Eggen et al.
2025/0367431 A1 12/2025 Baumbach et al.

FOREIGN PATENT DOCUMENTS

CN 1192351 A 9/1998
CN 1222862 A 7/1999
CN 1202871 C 5/2005
CN 1661338 A 8/2005
CN 101128168 2/2008
CN 101208045 6/2008
CN 101214158 7/2008

(56) References Cited

FOREIGN PATENT DOCUMENTS

| | | | | |
|---|---|---|---|---|
| CN | 101351237 | | 1/2009 | |
| CN | 101448535 | | 6/2009 | |
| CN | 101460094 | | 6/2009 | |
| CN | 101579233 | | 11/2009 | |
| CN | 201437016 | | 4/2010 | |
| CN | 101711683 | | 5/2010 | |
| CN | 201658687 | | 12/2010 | |
| CN | 102421372 | | 4/2012 | |
| CN | 102803923 | | 11/2012 | |
| CN | 103143072 | | 6/2013 | |
| CN | 103328018 | | 9/2013 | |
| CN | 103857326 | | 6/2014 | |
| CN | 103942511 | | 7/2014 | |
| CN | 103957957 | | 7/2014 | |
| CN | 104105449 | | 10/2014 | |
| CN | 104188687 | | 12/2014 | |
| CN | 104274873 | | 1/2015 | |
| CN | 106104229 | | 11/2016 | |
| CN | 106333707 | | 1/2017 | |
| CN | 104888293 | | 3/2017 | |
| CN | 206007680 | | 3/2017 | |
| CN | 106776441 | | 5/2017 | |
| CN | 107530479 | | 1/2018 | |
| CN | 107632167 | | 1/2018 | |
| CN | 109939282 | | 6/2019 | |
| CN | 209790495 | | 12/2019 | |
| CN | 210020563 | | 2/2020 | |
| CN | 112168427 | | 1/2021 | |
| CN | 215841206 | | 2/2022 | |
| CN | 114886614 | | 8/2022 | |
| CN | 217828630 | | 11/2022 | |
| CN | 115916111 | | 4/2023 | |
| CN | 116271502 | | 6/2023 | |
| CN | 219250364 | | 6/2023 | |
| CN | 117959584 | | 5/2024 | |
| CN | 118320294 | | 7/2024 | |
| CN | 113769260 | | 9/2024 | |
| CN | 118717356 | | 10/2024 | |
| CN | 118920928 | | 11/2024 | |
| CN | 119033506 | | 11/2024 | |
| DE | 11 65 144 | | 3/1964 | |
| DE | 195 20 920 | | 12/1995 | |
| DE | 198 21 307 | | 10/1999 | |
| DE | 100 59 714 | | 5/2002 | |
| DE | 100 60 275 | | 6/2002 | |
| DE | 101 44 269 | | 3/2003 | |
| DE | 102 26 305 | | 10/2003 | |
| DE | 103 02 550 | | 8/2004 | |
| DE | 20 2005 020 288 | | 6/2007 | |
| DE | 10 2006 001 180 | | 9/2007 | |
| DE | 10 2009 007 216 | | 8/2010 | |
| DE | 10 2009 011 726 | | 9/2010 | |
| DE | 10 2009 025 464 | | 1/2011 | |
| DE | 10 2009 047 845 | | 3/2011 | |
| DE | 10 2011 106 142 | | 12/2012 | |
| DE | 10 2012 200 912 | | 7/2013 | |
| DE | 20 2011 110 389 | | 9/2013 | |
| DE | 11 2012 005 944 | | 12/2014 | |
| DE | 20 2013 007 408 | | 12/2014 | |
| DE | 10 2015 004 177 | | 10/2015 | |
| DE | 10 2016 106 683 | | 10/2016 | |
| DE | 10 2015 219 263 | | 4/2017 | |
| DE | 10 2015 222 199 | | 5/2017 | |
| DE | 10 2016 225 862 | | 6/2017 | |
| DE | 20 2015 009 422 | | 7/2017 | |
| DE | 10 2016 203 172 | | 8/2017 | |
| DE | 10 2012 207 042 | | 9/2017 | |
| DE | 10 2016 013 334 | | 4/2018 | |
| DE | 10 2017 213 475 | | 2/2019 | |
| DE | 10 2018 204 604 | | 10/2019 | |
| DE | 10 2018 204 610 | | 10/2019 | |
| DE | 10 2018 206 714 | | 11/2019 | |
| DE | 10 2018 206 724 | | 11/2019 | |
| DE | 10 2018 206 725 | | 11/2019 | |
| DE | 10 2018 206 727 | | 11/2019 | |
| DE | 10 2018 206 731 | | 11/2019 | |
| DE | 10 2018 206 750 | | 11/2019 | |
| DE | 10 2018 206 754 | | 11/2019 | |
| DE | 10 2018 206 758 | | 11/2019 | |
| DE | 10 2018 208 536 | | 12/2019 | |
| DE | 10 2018 208 862 | | 12/2019 | |
| DE | 10 2018 208 916 | | 12/2019 | |
| DE | 10 2018 208 927 | | 12/2019 | |
| DE | 10 2018 208 945 | | 12/2019 | |
| DE | 10 2018 210 076 | | 12/2019 | |
| DE | 10 2018 212 153 | | 1/2020 | |
| DE | 10 2018 213 151 | | 2/2020 | |
| DE | 10 2018 213 350 | | 2/2020 | |
| DE | 10 2018 220 658 | | 6/2020 | |
| DE | 10 2018 222 505 | | 6/2020 | |
| DE | 10 2020 102 473 | | 8/2021 | |
| DE | 11 2020 003 151 | | 3/2022 | |
| EP | 0 794 411 | | 9/1997 | |
| EP | 0 916 359 | | 5/1999 | |
| EP | 0 930 086 | | 7/1999 | |
| EP | 1 062 959 | | 12/2000 | |
| EP | 1 339 443 | | 11/2001 | |
| EP | 1 011 803 | | 9/2004 | |
| EP | 1 354 606 | | 6/2006 | |
| EP | 2 143 385 | | 1/2010 | |
| EP | 2 175 770 | | 4/2010 | |
| EP | 2 187 807 | | 6/2012 | |
| EP | 2 570 143 | | 3/2013 | |
| EP | 2 401 003 | | 10/2013 | |
| EP | 2 752 209 | | 7/2014 | |
| EP | 2 782 210 | | 9/2014 | |
| EP | 1 871 441 | | 11/2014 | |
| EP | 2 859 911 | | 4/2015 | |
| EP | 2 966 753 | | 1/2016 | |
| EP | 2 213 227 | | 8/2016 | |
| EP | 2 835 141 | | 8/2016 | |
| EP | 2 454 799 | | 9/2016 | |
| EP | 3 088 016 | | 11/2016 | |
| EP | 2 585 129 | | 3/2017 | |
| EP | 2 709 689 | | 4/2017 | |
| EP | 3 220 505 | | 9/2017 | |
| EP | 2 945 661 | | 11/2017 | |
| EP | 2 136 861 | | 12/2017 | |
| EP | 3 020 426 | | 12/2017 | |
| EP | 3 287 154 | | 2/2018 | |
| EP | 3 205 359 | | 8/2018 | |
| EP | 3 205 360 | | 8/2018 | |
| EP | 3378421 | A1 * | 9/2018 | ......... A61B 17/3423 |
| EP | 3 389 738 | | 8/2019 | |
| EP | 3 536 360 | | 9/2019 | |
| EP | 2 505 090 | | 12/2019 | |
| EP | 3 668 560 | | 6/2020 | |
| EP | 3 720 520 | | 10/2020 | |
| EP | 3 753 594 | | 12/2020 | |
| EP | 3 357 523 | | 1/2021 | |
| EP | 3 423 126 | | 2/2021 | |
| EP | 3 490 628 | | 2/2021 | |
| EP | 3 198 677 | | 3/2021 | |
| EP | 3 248 647 | | 3/2021 | |
| EP | 3 436 106 | | 3/2021 | |
| EP | 3 487 548 | | 3/2021 | |
| EP | 3 509 661 | | 3/2021 | |
| EP | 3 515 523 | | 3/2021 | |
| EP | 3 528 863 | | 3/2021 | |
| EP | 3 615 103 | | 3/2021 | |
| EP | 4 271 461 | | 3/2021 | |
| EP | 3 436 105 | | 4/2021 | |
| EP | 3 116 407 | | 5/2021 | |
| EP | 3 131 600 | | 6/2021 | |
| EP | 3 131 615 | | 6/2021 | |
| EP | 3 827 876 | | 6/2021 | |
| EP | 2 608 731 | | 7/2021 | |
| EP | 3 463 505 | | 9/2021 | |
| EP | 3 884 970 | | 9/2021 | |
| EP | 2 599 510 | | 10/2021 | |
| EP | 3 003 421 | | 10/2021 | |
| EP | 3 027 241 | | 10/2021 | |
| EP | 3 077 018 | | 10/2021 | |
| EP | 3 485 936 | | 10/2021 | |

(56) References Cited

FOREIGN PATENT DOCUMENTS

| | | |
|---|---|---|
| EP | 3 668 561 | 10/2021 |
| EP | 3 164 168 | 12/2021 |
| EP | 3 344 129 | 12/2021 |
| EP | 3 539 613 | 2/2022 |
| EP | 2 858 718 | 3/2022 |
| EP | 3 624 867 | 3/2022 |
| EP | 3 651 822 | 3/2022 |
| EP | 3 689 389 | 3/2022 |
| EP | 3 737 436 | 3/2022 |
| EP | 3 972 661 | 3/2022 |
| EP | 3 755 237 | 4/2022 |
| EP | 3 984 589 | 4/2022 |
| EP | 3 654 006 | 5/2022 |
| EP | 3 497 775 | 7/2022 |
| EP | 3 737 310 | 7/2022 |
| EP | 2 999 400 | 8/2022 |
| EP | 3 711 788 | 8/2022 |
| EP | 2 654 883 | 9/2022 |
| EP | 3 485 819 | 9/2022 |
| EP | 3 694 573 | 9/2022 |
| EP | 3 600 477 | 10/2022 |
| EP | 3 897 768 | 10/2022 |
| EP | 3 808 408 | 11/2022 |
| EP | 3 858 422 | 11/2022 |
| EP | 2 892 583 | 1/2023 |
| EP | 3 370 797 | 1/2023 |
| EP | 3 597 231 | 1/2023 |
| EP | 3 668 562 | 1/2023 |
| EP | 3 856 275 | 1/2023 |
| EP | 3 003 420 | 2/2023 |
| EP | 3 397 299 | 2/2023 |
| EP | 3 046 594 | 3/2023 |
| EP | 3 938 005 | 4/2023 |
| EP | 3 946 511 | 4/2023 |
| EP | 3 685 562 | 5/2023 |
| EP | 3 826 104 | 5/2023 |
| EP | 3 397 298 | 7/2023 |
| EP | 3 809 959 | 7/2023 |
| EP | 2 072 150 | 9/2023 |
| EP | 2 961 984 | 9/2023 |
| EP | 3 352 808 | 9/2023 |
| EP | 3 768 156 | 9/2023 |
| EP | 4 052 754 | 10/2023 |
| EP | 3 157 596 | 11/2023 |
| EP | 3 766 428 | 11/2023 |
| EP | 3 781 027 | 11/2023 |
| EP | 4 061 470 | 11/2023 |
| EP | 4 070 720 | 11/2023 |
| EP | 3 449 958 | 12/2023 |
| EP | 3 687 596 | 12/2023 |
| EP | 3 768 340 | 12/2023 |
| EP | 3 801 675 | 1/2024 |
| EP | 3 566 636 | 2/2024 |
| EP | 3 634 526 | 2/2024 |
| EP | 3 768 347 | 2/2024 |
| EP | 3 790 606 | 2/2024 |
| EP | 3 930 780 | 2/2024 |
| EP | 3 397 147 | 3/2024 |
| EP | 3 782 695 | 3/2024 |
| EP | 3 854 448 | 3/2024 |
| EP | 4 140 532 | 5/2024 |
| EP | 3 693 038 | 6/2024 |
| EP | 3 970 765 | 7/2024 |
| EP | 3 854 444 | 9/2024 |
| EP | 3 793 674 | 10/2024 |
| EP | 3 618 885 | 11/2024 |
| EP | 3 809 960 | 12/2024 |
| EP | 3 854 446 | 2/2025 |
| EP | 4 429 754 | 2/2025 |
| EP | 3 970 785 | 3/2025 |
| EP | 4 429 753 | 3/2025 |
| EP | 3 950 043 | 5/2025 |
| EP | 3 899 964 | 6/2025 |
| EP | 3 948 888 | 6/2025 |
| EP | 3 965 845 | 6/2025 |
| EP | 4 039 319 | 6/2025 |
| EP | 4 297 672 | 7/2025 |
| EP | 3 668 559 | 8/2025 |
| EP | 3 848 088 | 8/2025 |
| EP | 4 218 556 | 9/2025 |
| EP | 3 911 227 | 1/2026 |
| EP | 4 201 467 | 1/2026 |
| ES | 2 913 485 | 6/2022 |
| GB | 2 504 177 | 1/2014 |
| JP | S59-080229 | 5/1984 |
| JP | S61-125329 | 6/1986 |
| JP | S62-113555 | 7/1987 |
| JP | S62-204733 | 9/1987 |
| JP | S62-282284 | 12/1987 |
| JP | S64-68236 | 3/1989 |
| JP | H02-055886 | 2/1990 |
| JP | H02-234750 | 9/1990 |
| JP | H05-079875 | 3/1993 |
| JP | H06-218044 | 8/1994 |
| JP | H07-047025 | 5/1995 |
| JP | H08-057042 | 3/1996 |
| JP | H08-066398 | 3/1996 |
| JP | H08-327527 | 12/1996 |
| JP | H10-052489 | 2/1998 |
| JP | H10-505766 | 6/1998 |
| JP | H11-178249 | 7/1999 |
| JP | H11-239617 | 9/1999 |
| JP | 2000-512191 | 9/2000 |
| JP | 2001-037728 | 2/2001 |
| JP | 2001-506140 | 5/2001 |
| JP | 2001-276213 | 10/2001 |
| JP | 2002-525175 | 8/2002 |
| JP | 2003-019197 | 1/2003 |
| JP | 2003-047656 | 2/2003 |
| JP | 2003-062065 | 3/2003 |
| JP | 2004-515278 | 5/2004 |
| JP | 2005-028137 | 2/2005 |
| JP | 2005-192687 | 7/2005 |
| JP | 2006-528006 | 12/2006 |
| JP | 2007-222644 | 9/2007 |
| JP | 2008-511414 | 4/2008 |
| JP | 2006-518249 | 8/2008 |
| JP | 2008-178690 | 8/2008 |
| JP | 2009-504290 | 2/2009 |
| JP | 2009-240348 | 10/2009 |
| JP | 2010-503495 | 2/2010 |
| JP | 2010-518907 | 6/2010 |
| JP | 4706886 | 6/2011 |
| JP | 2012-520157 | 9/2012 |
| JP | 2013-013216 | 1/2013 |
| JP | 2013-128792 | 7/2013 |
| JP | 2014-524274 | 9/2014 |
| JP | 2015-514529 | 5/2015 |
| JP | 2015-514531 | 5/2015 |
| JP | 2015-515429 | 5/2015 |
| JP | 2015-122448 | 7/2015 |
| JP | 2015-527172 | 9/2015 |
| JP | 2015-181800 | 10/2015 |
| JP | 2016-002466 | 1/2016 |
| JP | 2016-509950 | 4/2016 |
| JP | 2017-500932 | 1/2017 |
| JP | 2017-176719 | 10/2017 |
| JP | 2017-532084 | 11/2017 |
| JP | 2018-046708 | 3/2018 |
| JP | 2019-508128 | 3/2019 |
| JP | 2019-523110 | 8/2019 |
| JP | 2020-072985 | 5/2020 |
| JP | 2019-509141 | 2/2022 |
| KR | 10-1185112 | 9/2012 |
| WO | WO1989006513 A1 * | 1/1989 |
| WO | WO 92/015239 | 9/1992 |
| WO | WO 94/009835 | 5/1994 |
| WO | WO 98/043688 | 10/1998 |
| WO | WO 00/033047 | 6/2000 |
| WO | WO 2006/122001 | 11/2006 |
| WO | WO 2008/106103 | 9/2008 |
| WO | WO 2009/023905 | 2/2009 |
| WO | WO 2009/029977 | 3/2009 |
| WO | WO 2010/042054 | 4/2010 |

(56) References Cited

FOREIGN PATENT DOCUMENTS

| | | |
|---|---|---|
| WO | WO 2010/142286 | 12/2010 |
| WO | WO 2010/143272 | 12/2010 |
| WO | WO 2011/007300 | 1/2011 |
| WO | WO 2012/018917 | 2/2012 |
| WO | WO 2012/112378 | 8/2012 |
| WO | WO 2012/147061 | 11/2012 |
| WO | WO 2013/160443 | 10/2013 |
| WO | WO 2013/164831 | 11/2013 |
| WO | WO 2014/042925 | 3/2014 |
| WO | WO 2014/141284 | 9/2014 |
| WO | WO 2014/165635 | 10/2014 |
| WO | WO 2015/085220 | 6/2015 |
| WO | WO 2015/152732 | 10/2015 |
| WO | WO 2016/001284 | 1/2016 |
| WO | WO 2016/066180 | 5/2016 |
| WO | WO 2016/137743 | 9/2016 |
| WO | WO 2017/021846 | 2/2017 |
| WO | WO 2017/032751 | 3/2017 |
| WO | WO 2017/060257 | 4/2017 |
| WO | WO 2017/066257 | 4/2017 |
| WO | WO 2017/089440 | 6/2017 |
| WO | WO 2017/106190 | 6/2017 |
| WO | WO 2017/118738 | 7/2017 |
| WO | WO 2017/147291 | 8/2017 |
| WO | WO 2017/165372 | 9/2017 |
| WO | WO 2017/213032 | 12/2017 |
| WO | WO 2017/214118 | 12/2017 |
| WO | WO 2017/218349 | 12/2017 |
| WO | WO 2018/005228 | 1/2018 |
| WO | WO 2018/033799 | 2/2018 |
| WO | WO 2018/048800 | 3/2018 |
| WO | WO 2018/078615 | 5/2018 |
| WO | WO 2018/100192 | 6/2018 |
| WO | WO 2018/109038 | 6/2018 |
| WO | WO 2018/213089 | 11/2018 |
| WO | WO 2019/013794 | 1/2019 |
| WO | WO 2019/025258 | 2/2019 |
| WO | WO 2019/025259 | 2/2019 |
| WO | WO 2019/025260 | 2/2019 |
| WO | WO 2019/034670 | 2/2019 |
| WO | WO 2019/034775 | 2/2019 |
| WO | WO 2019/078723 | 4/2019 |
| WO | WO 2019/101786 | 5/2019 |
| WO | WO 2019/118371 | 6/2019 |
| WO | WO 2019/126721 | 6/2019 |
| WO | WO 2019/137911 | 7/2019 |
| WO | WO 2019/145253 | 8/2019 |
| WO | WO 2019/158996 | 8/2019 |
| WO | WO 2019/183247 | 9/2019 |
| WO | WO 2019/185511 | 10/2019 |
| WO | WO 2019/185512 | 10/2019 |
| WO | WO 2019/193604 | 10/2019 |
| WO | WO 2019/211400 | 11/2019 |
| WO | WO 2019/211405 | 11/2019 |
| WO | WO 2019/211410 | 11/2019 |
| WO | WO 2019/211413 | 11/2019 |
| WO | WO 2019/211414 | 11/2019 |
| WO | WO 2019/211415 | 11/2019 |
| WO | WO 2019/211416 | 11/2019 |
| WO | WO 2019/219883 | 11/2019 |
| WO | WO 2019/229210 | 12/2019 |
| WO | WO 2019/229220 | 12/2019 |
| WO | WO 2019/229224 | 12/2019 |
| WO | WO 2019/234145 | 12/2019 |
| WO | WO 2019/234146 | 12/2019 |
| WO | WO 2019/234148 | 12/2019 |
| WO | WO 2019/234149 | 12/2019 |
| WO | WO 2019/234151 | 12/2019 |
| WO | WO 2019/234152 | 12/2019 |
| WO | WO 2019/234153 | 12/2019 |
| WO | WO 2019/234161 | 12/2019 |
| WO | WO 2019/234162 | 12/2019 |
| WO | WO 2019/234163 | 12/2019 |
| WO | WO 2019/234164 | 12/2019 |
| WO | WO 2019/234166 | 12/2019 |
| WO | WO 2019/234167 | 12/2019 |
| WO | WO 2019/234169 | 12/2019 |
| WO | WO 2019/241556 | 12/2019 |
| WO | WO 2019/243582 | 12/2019 |
| WO | WO 2019/244031 | 12/2019 |
| WO | WO 2020/030686 | 2/2020 |
| WO | WO 2020/030706 | 2/2020 |
| WO | WO 2020/064707 | 4/2020 |
| WO | WO 2020/089429 | 5/2020 |
| WO | WO 2020/198280 | 10/2020 |
| WO | WO 2020/243756 | 12/2020 |
| WO | WO 2021/159001 | 8/2021 |
| WO | WO 2023/040546 | 12/2021 |
| WO | WO 2022/074136 | 4/2022 |
| WO | WO 2022/109590 | 5/2022 |
| WO | WO 2022/173970 | 8/2022 |
| WO | WO 2023/226779 | 9/2022 |
| WO | WO 2023/037162 | 3/2023 |
| WO | WO 2023/049813 | 3/2023 |
| WO | WO 2023/076869 | 5/2023 |
| WO | WO 2023/112044 | 6/2023 |
| WO | WO 2024/104184 | 5/2024 |

OTHER PUBLICATIONS

A. Vieli, "Doppler Flow Determination," British Journal of Anaesthesia, vol. 60, Supplement 1, 1988, pp. 107S-112S (Year: 1988).*

P Sinha et al., "Effect of mechanical assistance of the systemic ventricle in single ventricle circulation with cavopulmonary connection;" The Journal of Thoracic and Cardiovascular Surgery c vol. 147, No. 4, pp. 1271-1275 (Year: 2014).*

C.A.D. Leguy, E.M.H. Bosboom, A.P.G. Hoeks, F.N. van de Vosse, Assessment of blood volume flow in slightly curved arteries from a single velocity profile, Journal of Biomechanics, vol. 42, Issue 11, 2009, pp. 1664-1672, (Year: 2009).*

E. Walser, "Venous access ports: indications, implantation technique, follow-up, and complications;" Cardiovasc Intervent Radiol. Aug. 2012;35(4):751-64. doi: 10.1007/s00270-011-0271-2. Epub Sep. 16, 2011 (Abstract Only) (Year: 2011).*

Radiologyinfo.org, "Subcutaneous Port," https://www.radiologyinfo.org/en/glossary?id=ezNFREEzNEFFLTI5OTAtNDVFNy04MkVBLTA1RDVGMDdBMzNFRH0=&i=1&b=0&modal=1#:~:text=Definition%3A%20subcutaneous%20port-,subcutaneous%20port,patient's%20bloodstream%20on%20regular%20basis, accessed Sep. 2, 2025 (Year: 2025).*

Hertz Ph.D. et al, "Ultrasonic Engineering in Heart Diagnosis", The American Journal of Cardiology, Jan. 1967, vol. 19, No. 1, pp. 6-17.

International Preliminary Report on Patentability and Written Opinion received in PCT Application No. PCT/EP2019/064782, dated Dec. 17, 2020 in 7 pages.

International Search Report and Written Opinion received in PCT Application No. PCT/EP2019/064782, dated Sep. 9, 2019 in 12 pages.

Kong et al., "A Stein Equation Approach for Solutions to the Diophantine Equations," 2010 Chinese Control and Decision Conference, Xuzhou, May 26, 2010, pp. 3024-3028.

Koseli et al., "Online Viscosity Measurement of Complex Solutions Using Ultrasound Doppler Velocimetry", Turk J Chem, Jan. 2006, vol. 30, pp. 297-305.

McCormick et al., "Resolution of a 2/spl pi/ Ambiguity Problem in Multiple Frequency Spectral Estimation," in IEEE Transactions on Aerospace and Electronic Systems, Jan. 1995, vol. 31, No. 1, pp. 2-8.

Syrmos et al., "A Generalized Bezout Equation in Output Feedback Design," Proceedings of the 31st IEEE Conference on Decision and Control, Tucson, AZ, USA, Dec. 1992, vol. 4, pp. 3590-3594.

Udesen et al., "A Simple Method to Reduce Aliasing Artifacts in Color Flow Mode Imaging", IEEE Ultrasonics Symposium, 2005, Rotterdam, The Netherlands, Sep. 18-21, 2005, pp. 1352-1355.

Lombardi et al., "Flow Rate Profiler: an instrument to measure blood velocity profiles", Ultrasonics, 2001, vol. 39, pp. 143-150.

Mushi et al., "Identification of Fluidic Element Models to Simulate the Short-Term Baroreflex", Proceedings of the 45th IEEE Conference on Decision & Control, San Diego, CA, Dec. 13-15, 2006, pp. 6.

(56) References Cited

OTHER PUBLICATIONS

"Understanding Hot-Wire Anemometry", Advanced Thermal Solutions, Inc., 2007, pp. 13-17.
Vollkron et al., "Advanced Suction Detection for an Axial Flow Pump", Artificial Organs, 2006, vol. 30, No. 9, pp. 665-670.
Vollkron et al., "Development of a Suction Detection System for Axial Blood Pumps", Artificial Organs, 2004, vol. 28, No. 8, pp. 709-716.
Yuanyuan et al., "Characteristics Analysis for Doppler Ultrasound Blood Flow Signals", China Medical Device Information, 5(1), Feb. 28, 1999, pp. 36-42.
Zhang, Dabiao et al., "Design of Microwave Velocity and Distance Monitor System", Instrument Technique and Sensor, Hebei Normal University, Apr. 25, 2004, pp. 3.
Murali, Akila, "Design of Inductive Coils for Wireless Power Transfer to Pediatric Implants", A graduate project submitted in partial fulfillment of the requirements for the degree of Master of Science in Electrical Engineering, California State University, Northridge, May 2018, pp. 37.
Chung et al., "Improved Efficiency Characteristics of Wireless Power Charging System for Superconducting MAGLEV Train Using Inserted Permanent Magnets," 2018 IEEE International Symposium on Electromagnetic Compatibility, 2018, pp. 564-567.
"ECG Electrodes product comparison chart," 3M.com, 2018, |https://multimedia.3m.com/mws/media/14908830/red-dot-ecg-electrodes-comparison-chart.pdf, accessed May 18, 2025, 1 page.
Eeckhout, Md, PhD, et al., "Handbook of Complications During Percutaneous Cardiovascular Interventions", 2007 Informa UK Ltd., Ch. 12, pp. 167-177.
HeartMate 3™ Left Ventricular Assist System, Instructions for Use, Thoratec Corporation, Aug. 2017, pp. 536. [Uploaded in 3 parts].
Mack-Haynes, Robin, "Fasteners Made Easy," New Mexico State University, https://pubs.nmsu.edu/_c/C232.pdf, accessed May 18, 2025, pp. 8.
Mullins, Charles E., Md, "Cardiac Catheterization in Congenital Heart Disease: Pediatric and Adult", Blackwell Futura, 2006, Chapters 3, 4 and 32, pp. 101.
Sigg et al., "Cardiac Electophysiology Methods and Models", Springer, Clinical Perspective: Electrophysiology in the Young and Patients with Congenital Heart Disease, Ch. 23, 2010, pp. 457-477.
Tan et al., "Surface Engineering and Patterning Using Parylene for Biological Applications." Materials, Mar. 15, 2010, vol. 3, No. 3, pp. 1803-1832.

* cited by examiner

IMPLANTABLE DEVICE FOR DETERMINING A FLUID VOLUME FLOW THROUGH A BLOOD VESSEL

BACKGROUND

Field

The invention relates to an implantable device for determining a fluid volume flow through a blood vessel, an arrangement, a method for determining a fluid volume flow through a blood vessel in the region of an implanted device, and the use of a device. The invention is used in particular for (fully) implanted left heart assist systems (LVAD [Left Ventricular Assist Device]).

Description of the Related Art

Implanted left heart assist systems (LVAD) exist mainly in two variants. On the one hand, there are (percutaneous) minimally-invasive left heart assist systems. The second variant are left heart assist systems invasively implanted under the rib cage. The first variant circulates blood directly from the left ventricle into the aorta, because the (percutaneous) minimally invasive left heart assist system is positioned in the center of the aortic valve. The second variant circulates the blood from the apical region from the left ventricle via a bypass tube into the aorta.

SUMMARY

The task of a cardiac assist system is to circulate blood. The so-called heart-time-volume (HTV, usually stated in liters per minute) has high clinical relevance in this case. In other words, the heart-time volume affects the total volume flow of blood from a ventricle, particularly from the left ventricle to the aorta. Accordingly, the initial task is to determine this parameter as a metrology value while a cardiac assist system is in operation.

Depending on the level of assistance, which describes the share of the volume flow from the ventricle to the aorta conveyed by a circulation means, such as a pump of the assist system, a certain volume flow reaches the aorta via the physiological path through the aortic valve. The heart-time volume or the total volume flow ($Q_{HTV}$) from the ventricle to the aorta is therefore usually the sum of the pump volume flow ($Q_p$) and the aortic valve volume flow ($Q_a$).

An established method for determining the heart-time volume ($Q_{HTV}$) in the clinical setting is the use of dilution methods, all of which, however, rely on a catheter inserted transcutaneously and therefore can only provide heart-time volume measurement data during cardiac surgery or directly thereafter during the subsequent stay in intensive care. An established method for measuring the pump volume flow ($Q_p$) is the correlation of the operating parameters of the assist system, predominantly the electrical power consumption, possibly supplemented by further physiological parameters, such as the blood pressure. The integration of dedicated ultrasound measurement technology into an assist system has also already been proposed. It should be noted here that the mentioned ultrasonic metrology only measures the pump volume flow and cannot record a bypass flow through the aortic valves past the assist system.

A (fully) implanted recording of the heart-time volume, i.e. of $Q_{HTV}$, in particular by the assist system itself, is not disclosed in the prior art. Fully implanted in this case in particular means that the means required for recording are completely in the patient's body and remain there. This makes it possible to record the heart-time volume even outside of heart surgery.

Proceeding from the foregoing, the invention is based on the task of specifying an implantable device or a method for improved flow detection in a blood vessel.

According to some embodiments, an implantable device is proposed herein for determining a fluid volume flow through a blood vessel, comprising:

- at least one sensor for detecting at least one flow parameter,
- a retaining means for retaining a vessel wall port in the region of a vessel wall of the blood vessel, wherein the retaining means is further formed to retain the at least one sensor in the region of the vessel wall.

The device can be implanted. Furthermore, the assist system is preferably fully implantable. In other words, this means in particular that the means required for recording, in particular the at least one ultrasonic sensor, are (completely) located in the body of the patient and remain there. In addition, the retaining means and the vessel wall port are also (completely) located and principally also remain in the patient's body. However, it is not mandatory for a supply cable and/or a control unit or the analysis unit of the device to be (completely) arranged in the patient's body. For example, the device can be implanted such that the analysis unit of the device is arranged on the skin of the patient or outside the body of the patient and a connection is established to the sensor arranged in the body. In other words, this connection, for example in the form of a supply cable, can lead out of the body.

The fluid volume flow through the blood vessel in particular indicates how much volume of the fluid per unit of time is transported or flows through a (specific and/or flow-carrying) blood vessel cross-section. In particular, the device is configured for determining a fluid volume flow through a blood vessel cross-section in the region of the device. The fluid volume flow is preferably a total fluid volume flow or the so-called heart-time volume (formula symbol: $Q_{HTV}$), which describes the total fluid volume from a ventricle. This total fluid volume flow ($Q_{HTV}$) is usually the sum of the so-called pump volume flow ($Q_p$) and the so-called aortic valve volume flow ($Q_A$). The pump volume flow ($Q_p$) generally quantifies the flow that flows (only) through the assist system itself, for example through a (inlet) cannula of the assist system. The aortic valve volume flow ($Q_A$) regularly quantifies the flow that flows past the assist system through the aortic valve.

The blood vessel is preferably an artery. The blood vessel can for example be the aorta, in particular the part of the aorta ascending to the aortic arch, or the pulmonary trunk (Truncus pulmonalis) in the two pulmonary arteries. If the device is used in connection with a left heart assist system, the blood vessel is preferably the aorta. If the device is used in connection with a right heart assist system, the blood vessel is preferably the pulmonary trunk (Truncus pulmonalis) in the two pulmonary arteries.

The device comprises at least one sensor for recording at least one flow parameter. The sensor can, for example, have at least one ultrasonic transducer, at least one radar antenna, and/or at least one laser source. In other words, this means, in particular, that the sensor can for example be formed in the manner of an ultrasonic sensor, a radar sensor and/or a laser Doppler sensor (laser Doppler velocimeter). The at least one flow parameter is preferably a flow velocity and/or a fluid volume flow, in particular a total fluid volume flow. If a flow velocity is recorded by means of the sensor, the flow velocity recorded for determining the fluid volume flow can for example be multiplied by a (flow carrying) blood vessel cross-section (in the region of the device).

In addition, the device comprises a retaining means for retaining a vessel wall port in the region of a vessel wall of the blood vessel. The vessel wall port is usually set up to form an artificial passage through the vessel wall of the blood vessel or to keep an artificial opening in the vessel wall open. In other words, this means in particular that the vessel wall port can be used to form an artificial passage through a vessel wall of a blood vessel or to keep open an artificial opening in the vessel wall. For example, the vessel wall port can be formed in the manner of a ring, which is inserted into or penetrates the vessel wall and is formed from a material that can be used for medical purposes. The retaining means is in particular formed to retain or secure the vessel wall port in its intended position (in relation to the vessel wall). Preferably, the retaining means is formed to retain the vessel wall port at a (specific) position along a blood vessel circumference and/or the flow direction in the vessel wall, preferably the (ascending) aorta or the pulmonary trunk (Truncus pulmonalis) in the two pulmonary arteries.

In addition, the retaining means is formed to retain the at least one sensor in the region of the vessel wall, in particular the aorta or the pulmonary trunk, in the two pulmonary arteries. By an arrangement in or on the aorta or in or on the pulmonary trunk in the two pulmonary arteries, it can be achieved in a particularly advantageous manner that the entire fluid volume flow (total fluid volume flow) from the respective (left or right) ventricle can be recorded by means of the sensor.

The device is advantageously formed for carrying out a method proposed here.

In other words, in particular also an implantable device for determining a fluid volume flow through a blood vessel can be proposed here, comprising:

- a vessel wall port with which an artificial passage can be formed through a vessel wall of a blood vessel,
- a retaining means for retaining a vessel wall port in the region of a vessel wall of the blood vessel,
- at least one sensor for recording at least one flow parameter, which is retained on the retaining means.

According to an advantageous embodiment, it is proposed that the sensor comprises an ultrasonic element. The ultrasonic element is preferably an ultrasonic transducer element. In particular, precisely or only one ultrasonic sensor is provided. The ultrasonic sensor preferably comprises precisely or only one ultrasonic transducer element. This is sufficient particularly if a pulsed Doppler measurement is to be performed or if the PWD method is to be used.

According to an advantageous embodiment, it is proposed that the sensor be formed to carry out a pulsed Doppler method. In other words, this means in particular that the sensor is formed to carry out a so-called Pulsed Wave Doppler (PWD) method. A PWD measurement cycle comprises in particular a sequence of a (defined) number of successively emitted ultrasonic pulses. A new ultrasonic pulse is usually sent out only if all (significant) echoes of an ultrasonic pulse sent out immediately beforehand have dissipated and/or were received.

According to an advantageous embodiment, it is proposed that the sensor be formed for recording a blood vessel flow-carrying cross-section. In other words, this means in particular that the sensor is formed to measure a flow-carrying blood vessel cross-section in the region of the device. In connection with an ultrasonic measurement, an analysis of the time of flight between the emitted pulse and the received vessel wall echo can for example be carried out. The spatial dimensions (within the blood vessel) can be inferred from this, in particular at a known speed of sound in the propagation medium. It can be specified that the flow-carrying blood vessel cross-section be recorded repeatedly. Alternatively, the flow-carrying blood vessel cross-section (which in the chronological mean generally exhibits no significant change versus time) can be recorded once and stored in a memory, for example of a control unit or an analysis unit.

According to an advantageous embodiment, it is proposed that the at least one sensor comprises two ultrasonic elements. The two ultrasonic elements are preferably positioned at an offset to one another in the direction of flow. In other words, this means in particular that one ultrasonic element is arranged upstream of the other ultrasonic element. Furthermore, the two ultrasonic elements are preferably arranged opposite each other and aligned facing each other. This allows a measurement to be carried out between the two ultrasonic elements in an advantageous manner, wherein the direction of propagation of the ultrasonic signals together with the (main) flow direction describes an angle of less than or greater than 90° (but not exactly 90°). The two ultrasonic elements are particularly preferably arranged opposite each other and aligned facing each other such that the connecting line between the two ultrasonic elements extends centrally through a cross-section of the flow-carrying blood vessel.

Instead of placing the ultrasonic elements opposite each other, the ultrasonic elements can also be positioned next to each other on one side of the blood vessel. In this case, a reflector is preferably specified on the opposite side of the blood vessel, which can reflect the sound pulses to the respectively receiving ultrasonic element.

Furthermore, it can be specified that the at least one sensor comprises more than two ultrasonic elements. The best-suited pairs of ultrasonic element elements can, for example, be identified with time of flight measurements, and the measurement can then be carried out with these.

According to an advantageous embodiment, it is proposed that the sensor can change a main beam direction the sensor. The sensor is preferably formed for carrying out beam steering.

According to an advantageous embodiment, it is proposed that the retaining means be formed in the form of a cuff that at least partially circumferentially enwraps the blood vessel. The cuff preferably circumferentially enwraps the blood vessel or a circumference of the blood vessel to at least 80% or even completely. Furthermore, the retaining means is preferably formed from a material suitable for medical purposes, for example using silicone.

According to an advantageous embodiment, it is proposed that the retaining means be formed to retain the at least one sensor in or on the vessel wall. For this purpose, the retaining means can form a pocket in which the sensor is accommodated. The retaining means is preferably formed to retain the at least one sensor on an outer side or an outer circumference of the vessel wall. The retaining means is particularly preferably formed to retain two ultrasonic elements such that they are arranged opposite one another and are aligned facing one another, so that the connecting line between the two ultrasonic elements extends centrally through a cross-section of the flow-carrying blood vessel.

According to an advantageous embodiment, it is proposed that the vessel wall port have a feed through for a (electrical) cable or an opening for a bypass line. For this purpose, the vessel wall port can be formed in the shape of a ring, which is inserted into or can penetrate the vessel wall and is in particular formed from a material that can be used for medical purposes. The bypass line is generally specified and formed to connect a left ventricle or an assist system connected to the left ventricle with an aorta by bypassing the aortic valve.

According to another aspect, an arrangement is proposed, comprising a device according to any of the above claims and an implantable vascular assist system. The arrangement can further comprise at least one supply cable, a control unit, and/or an analysis unit. The analysis unit can for example be connected to the sensor of the device (by signal technology). The control unit can, for example, be connected to the assist system and/or the analysis unit (by signal technology). In addition, it can be specified that the analysis unit is (additionally) integrated in the control unit.

The vascular assist system is preferably a cardiac assist system, particularly preferably a ventricular assist system. The assist system is regularly used to assist the conveyance of blood in the cardiovascular system of humans, or patients if applicable. The assist system can be arranged at least partially in a blood vessel. The blood vessel is, for example, the aorta, particularly in the case of a left heart assist system, or the pulmonary trunk (Truncus pulmonalis) into the two pulmonary arteries, particularly in the case of a right heart assist system. The support system is preferably arrangeable at the outlet of the left ventricle of the heart or the left ventricle. The assist system is particularly preferably arrangeable in the aortic valve position.

The assist system is preferably a left-ventricular heart assist system (LVAD) or a percutaneous, minimally invasive left heart assist system. Furthermore, it is preferred that the assist system can be fully implanted. In other words, this means in particular that the means required for conveying blood, in particular a flow machine of the assist system, are completely located in the body of the patient and remain there. However, it is not mandatory that a control unit or an analysis unit of the assist system is also arranged in the body of the patient. For example, the assist system can be implanted such that the control unit or the analysis unit is arranged on the skin of the patient or outside the body of the patient and a connection is established to the flow machine arranged in the body. The assist system is particularly preferably configured and/or suitable for being arranged at least partially in a ventricle, preferably in the left ventricle of a heart, and/or in an aorta, in particular in the aortic valve position.

The assist system furthermore preferably comprises a cannula, in particular an inlet cannula, a flow machine, such as a pump and/or an electric motor. The electric motor is in this case regularly a component of the flow machine. The (inlet) cannula is preferably configured such that in the implanted state, it can guide fluid from a (left) ventricle of a heart to the flow machine. The assist system is preferably elongated and/or tubular. The cannula and the flow machine are preferably arranged in the region of opposite ends of the assist system.

According to an advantageous embodiment, it is proposed that the vessel wall port of the device have a feed through for a (electrical) cable of the assist system or an opening for a bypass line of the assist system. A feed through for a cable of the assist system is provided in particular if the assist system is an (left heart) assist system implantable in aortic valve position. An opening for a bypass line of the assist system is specified in particular if the assist system is an apically implantable (left heart) assist system.

According to another aspect, a method for determining a fluid volume flow through a blood vessel in the region of an implanted device is proposed, comprising the following steps:

a) perform a measurement with at least one sensor of the device, which is retained with a retaining means for retaining a vessel wall port in the region of a vessel wall of the blood vessel,
b) provide a measurement result from step a),
c) determine the fluid volume flow using the measurement result provided in step b).

The method is preferably carried out with a device presented here and/or an arrangement presented here. A pulsed Doppler measurement is preferably carried out in step a). Furthermore, it is preferred that in step c) a flow velocity measured by means of the sensor is multiplied by a known or measured (by means of the sensor) blood vessel cross-section. Alternatively, a (calibration) data set stored in the sensor and/or in a control or analysis unit can for example be used in step c), the data set providing a direct relationship between the measurement result and the fluid volume flow.

According to another aspect, use of a device proposed here for determining a fluid volume flow through a blood vessel is proposed.

The details, features, and advantageous embodiments discussed in connection with the device can also occur accordingly in the arrangement, the method and/or the use presented here and vice versa. In this respect, reference is made in full to the discussion therein regarding the detailed characterization of the features.

BRIEF DESCRIPTION OF THE DRAWINGS

The solution presented here as well as its technical environment are explained in more detail below with reference to the figures. It is important to note that the invention is not limited by the shown exemplary embodiments. In particular, unless explicitly stated otherwise, it is also possible to extract partial aspects of the facts explained in the figures and to combine them with other components and/or insights from other figures and/or the present description. The following are shown schematically.

DETAILED DESCRIPTION

Figure 1:
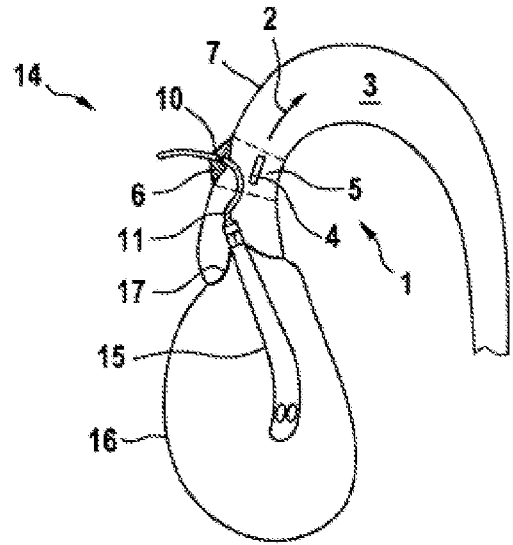
FIG. 1 an arrangement proposed herein.

FIG. 1 shows schematically an arrangement 14 proposed herein. The arrangement 14 comprises a device 1 proposed herein and an implantable vascular (here: ventricular) assist system 15. The arrangement is shown herein in an exemplary implanted state, wherein the assist system 15 passes through an aortic valve 17 and protrudes into a left ventricle 16. This illustrates an exemplary embodiment of an implanted left ventricular heart assist system 15 in the aortic valve position. In addition, the device 1 is arranged in the region of an ascending aorta 3.

The device 1 shown herein in an exemplary implanted state is formed to determine a fluid volume flow 2 through a blood vessel 3 (here the aorta). For this purpose, the device 1 comprises a sensor 4 for recording at least one flow parameter (here: the fluid volume flow 2) and a retaining means 5 for retaining a vessel wall port 6 in the region of a vessel wall 7 of the blood vessel 3. Here, the retaining means 5 is formed to retain the at least one sensor 4 in the region of the vessel wall 7.

The vessel wall port 6 of the device 1 in this case comprises a feed through 10 for a cable 11 of the assist system 15. The vessel wall port 6 or the feed through 10 in this case serves as an example for feeding out an electrical supply cable 11 for a (fully) implanted assist system 15 in the aortic valve position. In other words, the vessel wall port 6 forms in particular a port component of the device 1.

Figure 2:
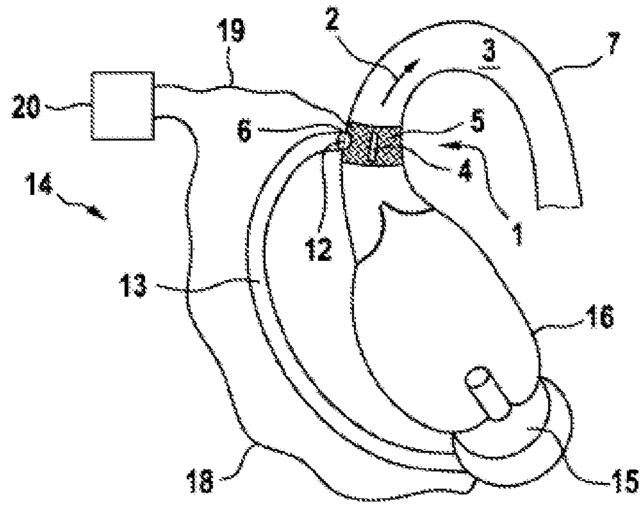
FIG. 2 a further arrangement proposed herein.

FIG. 2 shows schematically another arrangement 14 proposed herein. The arrangement 14 comprises a device 1 proposed herein, an implantable vascular (here: ventricular) assist system 15, and a control unit 20. The reference symbols are used uniformly so that reference can be made to the above explanations.

FIG. 2 illustrates an exemplary embodiment of an apically implanted left ventricular heart assist system 15. According to the illustration according to FIG. 2, the vessel wall port 6 of the device 1 has an opening 12 for a bypass line 13 of the assist system 15. The vessel wall port 6 or the opening 12 in this case serve as an example for recirculating a pump volume conveyed into the cardiovascular system by means of the assist system 1.

The control unit 20 can also be implanted (for fully implanted systems). However, this is not mandatory. In transcutaneous systems, for example, a first supply line 18 and a second supply line 19 can be guided through the skin to an extracorporeal control unit 20.

Figure 3:
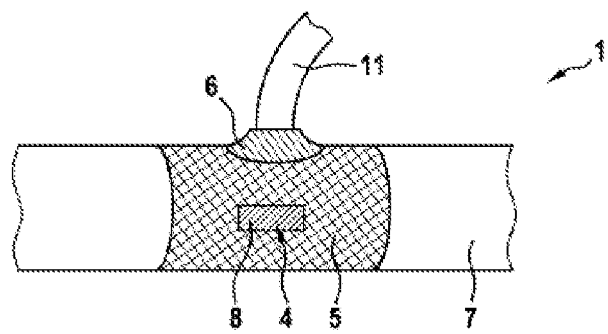
FIG. 3 a device proposed herein.

FIG. 3 shows schematically a device 1 proposed herein. The reference symbols are used uniformly so that reference can be made to the above explanations.

The retaining means 5 is in this case formed by way of example to retain the sensor 4 on the vessel wall 7. Furthermore, the retaining means 5 is formed by way of example in the shape of a cuff that at least partially circumferentially enwraps the blood vessel 3. The design as a cuff allows in an advantageous manner for a higher mechanical stability to be achieved and for the presence of installation space for sensors, for example ultrasonic transducers.

In FIG. 3, the sensor 4 comprises an ultrasonic element 8. In addition, the sensor 4 is formed for carrying out a pulsed Doppler method.

The flow calculation can be carried out using a single ultrasonic transducer 8 according to the Pulsed Wave Doppler method (PWD method). The ultrasonic transducer 8 sends an ultrasonic pulse and analyzes the phase progression of the sound energy back scattered on the cellular components of the blood in the time measurement window. In addition, large acoustic impedance differences, such as those occurring between blood and the aortic wall, can be detected in the transient reception signal.

Figure 4:
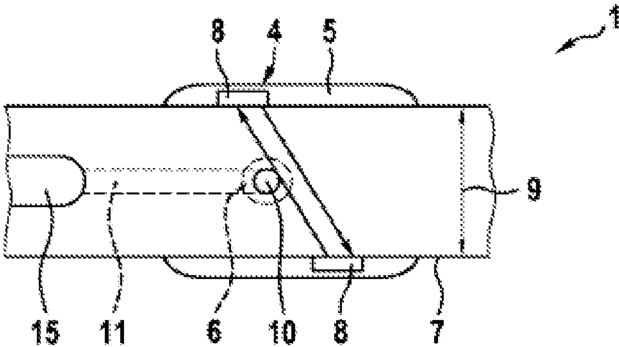
FIG. 4 a further device proposed herein in a cross-sectional view.

Furthermore, the sensor 4 is shown here by way of example for recording a flow-carrying blood vessel cross-section 9 (not shown here, cf. FIG. 4).

The spatial dimensions can be inferred from an analysis of the time of flight between the emitted pulse and the received aortic wall echo at a known speed of sound in the propagation medium. By combining both methods, it is possible to calculate the flow velocity with the Doppler method and to calculate the cross-sectional area of the aorta with the echo time of flight, so that the volume flow can be recorded or calculated with the best possible precision.

FIG. 4 shows schematically a further device 1 proposed herein in a cross-sectional view. The reference symbols are used uniformly so that reference can be made to the above explanations.

In FIG. 4, the one sensor 4 comprises two ultrasonic elements 8. The two ultrasonic elements 8 are positioned at an offset to one another in flow direction. Furthermore, the two ultrasonic elements 8 are arranged opposite each other and aligned facing each other. The illustration according to FIG. 4 illustrates by way of example the position of the ultrasonic transducers or ultrasonic elements 8 to each other.

FIG. 4 shows an exemplary embodiment wherein two ultrasonic transducers 8 are placed opposite the cuff 5. A pulsed ultrasonic method can also be used here. If the transducers 8 are not positioned orthogonally to the flow direction of the blood, the flow rate can be inferred based on the time of flight differences of the pulses from one ultrasonic element 8 to the other ultrasonic element 8 independently of the speed of sound in the medium. By means of the mean value of the signal time of flight, the geometry and thus the aortic cross-section 9 can also be inferred. It is advantageous for the method when low-focus ultrasonic transducers (ultrasonic elements) are used so that the method can remain operational even for poor positions of the sensors or the ultrasonic elements to each other (e.g. due to poor positioning or due to movement in the region of the aorta).

Figure 5:
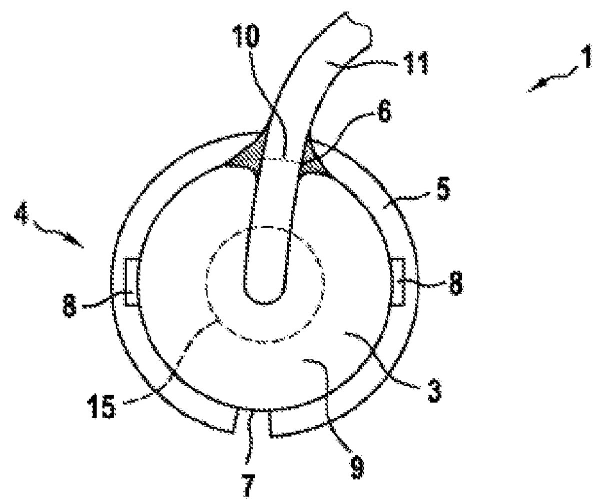
FIG. 5 the device according to FIG. 3 in a further cross-sectional view, and FIG. 6 a sequence of a method presented herein in a standard operating procedure.

FIG. 5 schematically shows the device according to FIG. 4 in a further cross-sectional view.

Here, it is shown by way of example that the two ultrasonic elements 8 are arranged opposite each other and aligned facing each other such that the connecting line between both elements 8 extends centrally through the cross-section of the blood vessel to be examined. In addition, the transducers 8 are positioned at an offset to each other along the flow direction, so that one pulse direction points downstream and the other pulse direction points upstream. For example, the angle of the main beam direction and the main flow direction is in the range of 0° to 85°, advantageously for example in the range of 45° (compromise between placement on the outer wall with a still high parallel portion of the main beam direction to the flow direction).

However, for inter-individual differences of the aortic cross-section 9 and a uniform cuff size, the transducers 8 can—if the cuff 5 is too small and the aortic cross-sectional area 9 is too large—migrate toward 12 o'clock, for example the ultrasonic element 8 shown on the left in FIG. 5 to 10 o'clock and the ultrasonic element 8 shown on the right in FIG. 5 to 2 o'clock. In particular, the ultrasonic measurement discussed above can also be carried out in this case by means of low-focused elements 8 with approximately spherical characteristics. In this case, however, a time of flight based cross-sectional area calculation could possibly have a corresponding error. Because the aortic cross-section 9 is generally on average not subject to major changes versus time, a (known) aortic cross-section, for example predetermined sonographically, can be stored in a calibration data memory (e.g. formed in the control unit 20 of the arrangement 14) as an alternative to the measurement using mean pulse time of flight.

As an alternative to a uniform cuff size, a plurality of devices that differ in the diameter of their retaining means can be specified, for example. During an implantation of the device, the device can then be selected with the appropriate retaining means diameter for the blood vessel.

Furthermore, it can be specified that the sensor 4 can change a main beam direction of the sensor 4. In this context, the measuring accuracy of the system can be further increased in the presence of a swirl or vortex in the blood flow by integrating one or more ultrasonic array transducers instead of single ultrasonic transducers. The measurement plane of the transducers can be pivoted by so-called beam steering, thus advantageously permitting a reconstruction of the complete three-dimensional flow vector field. The method can be generalized to a wave-based interaction means, i.e.—apart from the longitudinal waves present in ultrasound—the effect also occurs in the electromagnetic spectrum in transversal waves, for example of a radar sensor or a laser Doppler velocimeter. In addition to ultrasonic transducers, the integration of radar or laser Doppler sensors is therefore also advantageous, as these can (each) change their main beam direction.

Figure 6:
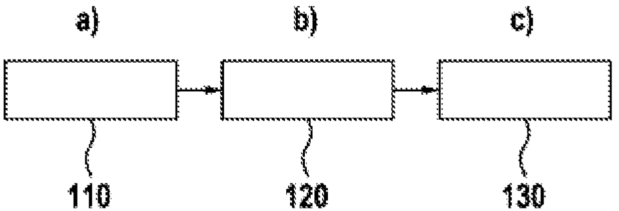

FIG. 6 schematically shows a sequence of a method presented herein in a standard operating procedure.

The method serves to determine a fluid volume flow through a blood vessel in the region of an implanted device. The illustrated sequence of the method steps a), b), and c) with the blocks 110, 120, and 130 results in a standard operating procedure. In block 110, a measurement is carried out with at least one sensor of the device, which is retained with a retaining means for retaining a vessel wall port in the region of a vessel wall of the blood vessel. A measurement result from step a) is provided in block 120. In block 130, the fluid volume flow is determined using the measurement result provided in step b).

The solution presented herein advantageously specifies a device, an arrangement, a method, and a use for determining the total cardiac output (HTV) of a patient with implanted left ventricular cardiac assist system (LVAD). The heart-time volume is an important parameter for assisting the human cardiovascular system with an assist system and can be (continuously) provided in a particularly advantageous manner with the solution proposed herein even outside of cardiac surgery and the subsequent intensive care medical treatment or during routine daily or continuous operation of the implanted assist system. In particular, this parameter (HTV) can be provided continuously as a control parameter for operating the assist system.

The solution proposed herein is based in particular on an integration of, for example, ultrasonic flow metrology into a retaining means for a vessel wall port, for example an aortic wall port as a feed-through for the connecting cable of a ventricular assist system. In particular when the device is located in the region of the aorta, both the blood flow generated by the assist system and the residual output capacity of the heart through the aortic valve past the assist system can thus be advantageously determined.

The solution presented herein in particular has one or more of the following advantages:

- For fully implanted assist systems, the thorax is opened to position an electronic control component. Access for attaching, for example, a silicone cuff around the aorta is therefore already provided.
- For (fully) implanted assist systems in the aortic valve position, the supply cable must be guided out of the aorta. The port required for this purpose is suitable as a cuff component for integrating flow metrology, so that no further components need to be integrated.
- Compared to devices without sensors, only the connection of the additional sensor cable is required during the implantation procedure.
- The solution allows continuous recording of the cardiac output in patients with a cardiac assist system.

The invention claimed is:

1. A device for determining a blood volume flow through a blood vessel, comprising:

at least one sensor configured to detect at least one flow parameter of blood in the blood vessel, the blood vessel being in fluid communication with a pump of a cardiac assist system configured to be implanted in the blood vessel;

a cuff configured to at least partially encircle an exterior wall of the blood vessel and retain the at least one sensor in or on the exterior wall; and a vessel wall port coupled to the cuff, the vessel wall port shaped to penetrate the exterior wall of the blood vessel to receive a portion of the cardiac assist system therethrough, wherein the cuff comprises at least one opening configured to receive the vessel wall port and retain the vessel wall port in a desired circumferential position in or on the exterior wall.

2. The device according to claim 1, wherein the at least one sensor comprises an ultrasonic element.

3. The device according to claim 1, wherein the at least one sensor is configured to perform a pulsed Doppler measurement.

4. The device according to claim 1, wherein the at least one sensor is configured to record a blood vessel cross-section of the blood vessel.

5. The device according to claim 1, wherein the at least one sensor comprises two ultrasonic elements.

6. The device according to claim 5, wherein the two ultrasonic elements are offset relative to one another in a flow direction of the blood in the blood vessel.

7. The device according to claim 5, wherein the two ultrasonic elements are arranged opposite each other and aligned facing each other.

8. The device according to claim 1, wherein the at least one sensor is configured to change a main beam direction of the at least one sensor.

9. The device according to claim 1, wherein the cuff is configured to position the vessel wall port to receive the portion of the cardiac assist system.

10. The device according to claim 1, wherein the vessel wall port comprises a feed-through for a cable of the cardiac assist system.

11. The device according to claim 1, wherein the vessel wall port comprises an opening for a bypass line of the cardiac assist system.

12. A system comprising:

a cardiac assist system configured to be implanted within a blood vessel; and a device configured to determine blood volume flow of blood within the blood vessel, the device comprising:

at least one sensor configured to detect at least one flow parameter of the blood in the blood vessel;

a cuff configured to at least partially encircle an exterior wall of the blood vessel and retain the at least one sensor in or on the exterior wall; and a vessel wall port coupled to the cuff, the vessel wall port shaped to penetrate the exterior wall of the blood vessel to receive a portion of the cardiac assist system therethrough, wherein the cuff comprises at least one opening configured to receive the vessel wall port and retain the vessel wall port in a desired circumferential position in or on the exterior wall.

13. The system according to claim 12, wherein the cuff is configured to position the vessel wall port to receive the portion of the cardiac assist system.

14. The system according to claim 12, wherein the vessel wall port comprises a feed-through for a cable of the cardiac assist system.

15. The system according to claim 12, wherein the vessel wall port comprises an opening for a bypass line of the cardiac assist system.

16. A method for determining a blood volume flow through a blood vessel having a cardiac assist system configured to be implanted therein, the method comprising:

performing a measurement with at least one sensor of a device, the device comprising:

a cuff configured to at least partially encircle an exterior wall of the blood vessel and retain the at least one sensor in or on the exterior wall; and a vessel wall port coupled to the cuff, the vessel wall port shaped to penetrate the exterior wall of the blood vessel to receive a portion of the cardiac assist system therethrough, wherein the cuff comprises at least one opening configured to receive the vessel wall port and retain the vessel wall port in a desired circumferential position in or on the exterior wall; and determining the blood volume flow based at least in part on the measurement.

17. The method according to claim 16, wherein the vessel wall port comprises a feed-through for a cable of the cardiac assist system.

18. The method according to claim 16, wherein the vessel wall port comprises an opening for a bypass line of the cardiac assist system.

* * * * *